(12) United States Patent
Klepfer et al.

(10) Patent No.: US 11,305,127 B2
(45) Date of Patent: Apr. 19, 2022

(54) VFA DELIVERY AND IMPLANT REGION DETECTION

(71) Applicant: Medtronic, Inc., Minneapolis, MN (US)

(72) Inventors: Ruth N. Klepfer, St. Louis Park, MN (US); Zhongping Yang, Woodbury, MN (US); Andrea J. Asleson, Maple Grove, MN (US); Nathan A. Grenz, North Oaks, MN (US); Kaileigh E. Rock, Minneapolis, MN (US)

(73) Assignee: Medtronic Inc., Minneapolis, MN (US)

( * ) Notice: Subject to any disclaimer, the term of this patent is extended or adjusted under 35 U.S.C. 154(b) by 124 days.

(21) Appl. No.: 16/812,321

(22) Filed: Mar. 8, 2020

(65) Prior Publication Data

US 2021/0060340 A1 Mar. 4, 2021

Related U.S. Application Data

(60) Provisional application No. 62/891,599, filed on Aug. 26, 2019.

(51) Int. Cl.
*A61N 1/368* (2006.01)
*A61N 1/05* (2006.01)
*A61N 1/362* (2006.01)
*A61N 1/375* (2006.01)

(52) U.S. Cl.
CPC ......... *A61N 1/3684* (2013.01); *A61N 1/0573* (2013.01); *A61N 1/3627* (2013.01); *A61N 1/3756* (2013.01); *A61N 1/37518* (2017.08)

(58) Field of Classification Search
None
See application file for complete search history.

(56) References Cited

U.S. PATENT DOCUMENTS

| | | | |
|---|---|---|---|
| 3,835,864 A | 9/1974 | Rasor et al. |
| 3,865,118 A | 2/1975 | Bures |
| 3,943,936 A | 3/1976 | Rasor et al. |
| 3,949,757 A | 4/1976 | Sabel |
| 4,142,530 A | 3/1979 | Wittkampf |
| 4,151,513 A | 4/1979 | Menken et al. |
| 4,157,720 A | 6/1979 | Greatbatch |

(Continued)

FOREIGN PATENT DOCUMENTS

| | | |
|---|---|---|
| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)

(Continued)

*Primary Examiner* — Brian T Gedeon
(74) *Attorney, Agent, or Firm* — Mueting Raasch Group

(57) ABSTRACT

A method includes locating the triangle of Koch region in the right atrium of a patient's heart; securing at least one electrode of an implantable lead or device to cardiac tissue from the triangle of Koch region to deliver ventricle-from-atrium (VfA) cardiac therapy; and testing the location or depth of the at least one electrode to configure VfA cardiac therapy. Locating the target implant region in the triangle of Koch region may include detecting an atrial slow pathway potential (ASP) or atrial pacing output.

20 Claims, 14 Drawing Sheets

(56) References Cited

U.S. PATENT DOCUMENTS

| | | |
|---|---|---|
| RE30,366 E | 8/1980 | Rasor et al. |
| 4,243,045 A | 1/1981 | Mass |
| 4,250,884 A | 2/1981 | Hartlaub et al. |
| 4,256,115 A | 3/1981 | Bilitch |
| 4,263,919 A | 4/1981 | Levin |
| 4,280,502 A | 7/1981 | Baker, Jr. et al. |
| 4,289,144 A | 9/1981 | Gilman |
| 4,310,000 A | 1/1982 | Lindemans |
| 4,312,354 A | 1/1982 | Walters |
| 4,323,081 A | 4/1982 | Wiebusch |
| 4,332,259 A | 6/1982 | McCorkle, Jr. |
| 4,357,946 A | 11/1982 | Dutcher et al. |
| 4,365,639 A | 12/1982 | Goldreyer |
| 4,374,382 A | 2/1983 | Markowitz et al. |
| 4,393,883 A | 7/1983 | Smyth et al. |
| 4,440,173 A | 4/1984 | Hudziak et al. |
| 4,476,868 A | 10/1984 | Thompson |
| 4,479,500 A | 10/1984 | Smits |
| 4,522,208 A | 6/1985 | Buffet |
| 4,537,200 A | 8/1985 | Widrow |
| 4,546,777 A | 10/1985 | Groch et al. |
| 4,556,063 A | 12/1985 | Thompson et al. |
| 4,562,841 A | 1/1986 | Brockway et al. |
| 4,574,814 A | 3/1986 | Buffet |
| 4,593,702 A | 6/1986 | Ski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,830,006 A | 5/1989 | Haluska et al. |
| 4,858,610 A | 8/1989 | Callaghan et al. |
| 4,865,037 A | 9/1989 | Chin et al. |
| 4,886,064 A | 12/1989 | Strandberg |
| 4,887,609 A | 12/1989 | Cole, Jr. |
| 4,928,688 A | 5/1990 | Mower |
| 4,953,564 A | 9/1990 | Berthelsen |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,107,850 A | 4/1992 | Olive |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grievous et al. |
| 5,133,353 A | 7/1992 | Hauser |
| 5,144,950 A | 9/1992 | Stoop et al. |
| 5,154,170 A | 10/1992 | Bennett et al. |
| 5,170,784 A | 12/1992 | Ramon et al. |
| 5,174,289 A | 12/1992 | Cohen |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,255,692 A | 10/1993 | Neubauer et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,594 A | 6/1994 | Limousin et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,554,177 A | 9/1996 | Kieval et al. |
| 5,562,711 A | 10/1996 | Yerich et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,140 A | 3/1998 | Salo et al. |
| 5,728,154 A | 3/1998 | Crossett et al. |
| 5,741,314 A | 4/1998 | Daly et al. |
| 5,741,315 A | 4/1998 | Lee et al. |
| 5,749,909 A | 5/1998 | Schroeppel et al. |
| 5,752,976 A | 5/1998 | Duffin et al. |
| 5,752,977 A | 5/1998 | Grievous et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,817,130 A | 10/1998 | Cox et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,928,271 A | 7/1999 | Hess et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |

(56) References Cited

U.S. PATENT DOCUMENTS

| | | |
|---|---|---|
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,132,456 A | 10/2000 | Sommer et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,903 B1 | 9/2001 | Rosenthal et al. |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,393,316 B1 | 5/2002 | Gillberg et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardv |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,508,771 B1 | 1/2003 | Padmanabhan et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,544,270 B1 | 4/2003 | Zhang |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,623,518 B2 | 9/2003 | Thompson et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,754,528 B2 | 6/2004 | Bardy et al. |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,869,404 B2 | 3/2005 | Schulhauser et al. |
| 6,871,095 B2 | 3/2005 | Stahmann et al. |
| 6,871,096 B2 | 3/2005 | Hill |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,931,286 B2 | 8/2005 | Sigg et al. |
| 6,934,585 B1 | 8/2005 | Schloss et al. |
| 6,941,169 B2 | 9/2005 | Pappu |
| 6,957,107 B2 | 10/2005 | Rogers et al. |
| 6,978,176 B2 | 12/2005 | Lattouf |
| 6,980,675 B2 | 12/2005 | Evron et al. |
| 6,985,773 B2 | 1/2006 | Von Arx et al. |
| 6,990,375 B2 | 1/2006 | Kloss et al. |
| 6,993,389 B2 | 1/2006 | Ding et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,176 B2 | 3/2006 | Ding et al. |
| 7,013,178 B2 | 3/2006 | Reinke et al. |
| 7,027,871 B2 | 4/2006 | Burnes et al. |
| 7,031,711 B2 | 4/2006 | Brown et al. |
| 7,031,771 B2 | 4/2006 | Brown et al. |
| 7,035,684 B2 | 4/2006 | Lee et al. |
| 7,050,849 B2 | 5/2006 | Echt et al. |
| 7,060,031 B2 | 6/2006 | Webb et al. |
| 7,063,693 B2 | 6/2006 | Guenst |

(56) References Cited

U.S. PATENT DOCUMENTS

| | | |
|---|---|---|
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,284 B2 | 2/2007 | Burnes et al. |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,231,248 B2 | 6/2007 | Kramer et al. |
| 7,231,253 B2 | 6/2007 | Tidemand et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,286,866 B2 | 10/2007 | Okerlund et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,307,321 B1 | 12/2007 | Avanzino |
| 7,308,297 B2 | 12/2007 | Reddy et al. |
| 7,308,299 B2 | 12/2007 | Burrell et al. |
| 7,310,556 B2 | 12/2007 | Bulkes |
| 7,317,950 B2 | 1/2008 | Lee |
| 7,319,905 B1 | 1/2008 | Morgan et al. |
| 7,321,677 B2 | 1/2008 | Evron et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,346,381 B2 | 3/2008 | Okerlund et al. |
| 7,346,393 B2 | 3/2008 | Spinelli et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,454,248 B2 | 11/2008 | Burrell et al. |
| 7,496,409 B2 | 2/2009 | Greenhut et al. |
| 7,496,410 B2 | 2/2009 | Heil |
| 7,499,743 B2 | 3/2009 | Vass et al. |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,546,166 B2 | 6/2009 | Michels et al. |
| 7,558,626 B2 | 7/2009 | Corbucci |
| 7,558,631 B2 | 7/2009 | Cowan et al. |
| 7,565,190 B2 | 7/2009 | Okerlund et al. |
| 7,565,195 B1 | 7/2009 | Kroll et al. |
| 7,584,002 B2 | 9/2009 | Burnes et al. |
| 7,587,074 B2 | 9/2009 | Zarkh et al. |
| 7,590,455 B2 | 9/2009 | Heruth et al. |
| 7,599,730 B2 | 10/2009 | Hunter et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,613,500 B2 | 11/2009 | Vass et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,764 B2 | 12/2009 | Ding et al. |
| 7,630,767 B1 | 12/2009 | Poore et al. |
| 7,634,313 B1 | 12/2009 | Kroll et al. |
| 7,635,541 B2 | 12/2009 | Scott et al. |
| 7,637,867 B2 | 12/2009 | Zdeblick |
| 7,640,057 B2 | 12/2009 | Libbus et al. |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,657,313 B2 | 2/2010 | Rom |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,706,879 B2 | 4/2010 | Burnes et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,629 B2 | 6/2010 | Zarkh et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,047 B2 | 6/2010 | Okerlund et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,778,685 B2 | 8/2010 | Evron et al. |
| 7,778,686 B2 | 8/2010 | Vass et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,813,785 B2 | 10/2010 | Okerlund et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |

(56) References Cited

U.S. PATENT DOCUMENTS

| | | |
|---|---|---|
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,877,144 B2 | 1/2011 | Coles, Jr. et al. |
| 7,881,786 B2 | 2/2011 | Jackson |
| 7,881,791 B2 | 2/2011 | Sambelashvili et al. |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,902 B2 | 2/2011 | Rom |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,912,544 B1 | 3/2011 | Min et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,027 B2 | 4/2011 | Prakash et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,941,218 B2 | 5/2011 | Sambelashvili et al. |
| 7,945,333 B2 | 5/2011 | Jacobson |
| 7,946,997 B2 | 5/2011 | Hubinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,063 B2 | 8/2011 | Vass et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,002,718 B2 | 8/2011 | Buchholtz et al. |
| 8,010,191 B2 | 8/2011 | Zhu et al. |
| 8,010,209 B2 | 8/2011 | Jacobson |
| 8,014,861 B2 | 9/2011 | Zhu et al. |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,065 B2 | 10/2011 | Burnes et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,185 B2 | 11/2011 | Hunter et al. |
| 8,060,212 B1 | 11/2011 | Rios et al. |
| 8,065,018 B2 | 11/2011 | Haubrich et al. |
| 8,068,920 B2 | 11/2011 | Gaudiani |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,105,714 B2 | 1/2012 | Schmidt et al. |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,145,308 B2 | 3/2012 | Sambelashvili et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,428 B2 | 5/2012 | Kaiser et al. |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,590 B2 | 6/2012 | Sambelashvili et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,041 B2 | 7/2012 | Van Gelder et al. |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,014 B2 | 11/2012 | Maskara et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,027 B2 | 1/2013 | Spinelli et al. |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,383,269 B2 | 2/2013 | Scott et al. |
| 8,386,051 B2 | 2/2013 | Rys |
| 8,391,964 B2 | 3/2013 | Musley et al. |
| 8,391,981 B2 | 3/2013 | Mosesov |
| 8,391,990 B2 | 3/2013 | Smith et al. |
| 8,401,616 B2 | 3/2013 | Verard et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,406,899 B2 | 3/2013 | Reddy et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |

(56) References Cited

U.S. PATENT DOCUMENTS

| | | |
|---|---|---|
| 8,428,716 B2 | 4/2013 | Mullen et al. |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,467,871 B2 | 6/2013 | Maskara |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,509,916 B2 | 8/2013 | Byrd et al. |
| 8,515,559 B2 | 8/2013 | Roberts et al. |
| 8,521,268 B2 | 8/2013 | Zhang et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matoes |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,594,775 B2 | 11/2013 | Ghosh et al. |
| 8,612,002 B2 | 12/2013 | Faltys et al. |
| 8,615,310 B2 | 12/2013 | Khairkhahan et al. |
| 8,617,082 B2 | 12/2013 | Zhang et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,333 B2 | 1/2014 | Stadler et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,314 B2 | 3/2014 | Maskara et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | Dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,731,642 B2 | 5/2014 | Zarkh et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,750,994 B2 | 6/2014 | Ghosh et al. |
| 8,750,998 B1 | 6/2014 | Ghosh et al. |
| 8,755,884 B2 | 6/2014 | Demmer et al. |
| 8,758,365 B2 | 6/2014 | Bonner et al. |
| 8,768,459 B2 | 7/2014 | Ghosh et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,861,830 B2 | 10/2014 | Brada et al. |
| 8,868,186 B2 | 10/2014 | Kroll |
| 8,886,307 B2 | 11/2014 | Sambelashvili et al. |
| 8,886,311 B2 | 11/2014 | Anderson et al. |
| 8,886,339 B2 | 11/2014 | Faltys et al. |
| 8,903,473 B2 | 12/2014 | Rogers et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,948,883 B2 | 2/2015 | Eggen et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,033,996 B1 | 5/2015 | West |
| 9,037,262 B2 | 5/2015 | Regnier et al. |
| 9,042,984 B2 | 5/2015 | Demmer et al. |
| 9,072,872 B2 | 7/2015 | Asleson et al. |
| 9,072,911 B2 | 7/2015 | Hastings et al. |
| 9,072,913 B2 | 7/2015 | Jacobson |
| 9,101,281 B2 | 8/2015 | Reinert et al. |
| 9,119,959 B2 | 9/2015 | Rys et al. |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashbili et al. |
| 9,302,115 B2 | 4/2016 | Molin et al. |
| 9,320,446 B2 | 4/2016 | Gillberg et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |

(56) References Cited

U.S. PATENT DOCUMENTS

| | | |
|---|---|---|
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Regnier et al. |
| 9,457,193 B2 | 10/2016 | Klimovitch et al. |
| 9,474,457 B2 | 10/2016 | Ghosh et al. |
| 9,486,151 B2 | 11/2016 | Ghosh et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,517,336 B2 | 12/2016 | Eggen et al. |
| 9,522,276 B2 | 12/2016 | Shen et al. |
| 9,522,280 B2 | 12/2016 | Fishier et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,579,500 B2 | 2/2017 | Rys et al. |
| 9,623,234 B2 | 4/2017 | Anderson |
| 9,636,511 B2 | 5/2017 | Carney et al. |
| 9,643,014 B2 | 5/2017 | Zhang et al. |
| 9,675,579 B2 | 6/2017 | Rock et al. |
| 9,707,399 B2 | 7/2017 | Zielinski et al. |
| 9,724,519 B2 | 8/2017 | Demmer et al. |
| 9,789,319 B2 | 10/2017 | Sambelashvili |
| 9,808,628 B2 | 11/2017 | Sheldon et al. |
| 9,808,633 B2 | 11/2017 | Bonner et al. |
| 9,877,789 B2 | 1/2018 | Ghosh |
| 9,924,884 B2 | 3/2018 | Ghosh et al. |
| 10,004,467 B2 | 6/2018 | Lahm et al. |
| 10,064,567 B2 | 9/2018 | Ghosh et al. |
| 10,099,050 B2 | 10/2018 | Chen et al. |
| 10,166,396 B2 | 1/2019 | Schrock et al. |
| 10,251,555 B2 | 4/2019 | Ghosh et al. |
| 10,406,370 B1 | 9/2019 | Makharinsky |
| 10,456,581 B2 | 10/2019 | Liu et al. |
| 10,478,627 B2 | 11/2019 | Muessig |
| 10,850,107 B2 | 12/2020 | Li et al. |
| 10,850,108 B2 | 12/2020 | Li et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0004549 A1 | 1/2003 | Hill et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0083104 A1 | 5/2003 | Bonner et al. |
| 2003/0088278 A1 | 5/2003 | Bardy et al. |
| 2003/0092995 A1 | 5/2003 | Thompson |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0064158 A1 | 4/2004 | Klein et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0116878 A1* | 6/2004 | Byrd ................ A61N 1/056 604/263 |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 12/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0008210 A1 | 1/2005 | Evron et al. |
| 2005/0038477 A1 | 2/2005 | Kramer et al. |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0137629 A1 | 6/2005 | Dyjach et al. |
| 2005/0137671 A1 | 6/2005 | Liu et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0277990 A1 | 12/2005 | Ostroff et al. |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0074285 A1 | 4/2006 | Zarkh et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1* | 6/2006 | Cowan .............. A61N 1/3621 607/33 |
| 2006/0161061 A1 | 7/2006 | Echt et al. |
| 2006/0161205 A1 | 7/2006 | Mitrani et al. |
| 2006/0200002 A1 | 9/2006 | Guenst |
| 2006/0206151 A1 | 9/2006 | Lu |

(56) References Cited

U.S. PATENT DOCUMENTS

| | | |
|---|---|---|
| 2006/0212079 A1 | 9/2006 | Routh et al. |
| 2006/0235478 A1 | 10/2006 | Van Gelder et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0049975 A1 | 3/2007 | Cates et al. |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jaconson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0233216 A1 | 10/2007 | Liu et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2007/0299475 A1 | 12/2007 | Levin et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0103539 A1 | 5/2008 | Stegemann et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269816 A1 | 10/2008 | Prakash et al. |
| 2008/0269823 A1 | 10/2008 | Burnes et al. |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0099619 A1 | 4/2009 | Lessmeier et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | Jason |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0234412 A1 | 9/2009 | Sambelashvili |
| 2009/0234413 A1 | 9/2009 | Sambelashvili et al. |
| 2009/0234414 A1 | 9/2009 | Sambelashvili et al. |
| 2009/0234415 A1 | 9/2009 | Sambelashvili et al. |
| 2009/0248103 A1 | 10/2009 | Sambelashvili et al. |
| 2009/0259272 A1 | 10/2009 | Reddy et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0016914 A1 | 1/2010 | Mullen et al. |
| 2010/0016917 A1* | 1/2010 | Efimov ............... A61N 1/362 607/17 |
| 2010/0023078 A1 | 1/2010 | Dong et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0063375 A1 | 3/2010 | Kassab et al. |
| 2010/0063562 A1 | 3/2010 | Cowan et al. |
| 2010/0065871 A1 | 3/2010 | Govari et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0152798 A1 | 6/2010 | Sanghera et al. |
| 2010/0168761 A1 | 7/2010 | Kassab et al. |
| 2010/0168819 A1 | 7/2010 | Freeberg |
| 2010/0185250 A1 | 7/2010 | Rom |
| 2010/0198288 A1 | 8/2010 | Ostroff |
| 2010/0198291 A1 | 8/2010 | Sambelashvili et al. |
| 2010/0198304 A1 | 8/2010 | Wang |
| 2010/0217367 A1 | 8/2010 | Belson |
| 2010/0218147 A1 | 8/2010 | Ishikawa |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286541 A1 | 11/2010 | Musley et al. |
| 2010/0286626 A1 | 11/2010 | Petersen |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Ideblick et al. |
| 2011/0071586 A1 | 3/2011 | Jacobson |
| 2011/0077708 A1 | 3/2011 | Ostroff |
| 2011/0106202 A1 | 5/2011 | Ding et al. |
| 2011/0112398 A1 | 5/2011 | Zarkh et al. |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0190841 A1 | 8/2011 | Sambelashvili et al. |
| 2011/0196444 A1 | 8/2011 | Prakash et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |

(56) References Cited

U.S. PATENT DOCUMENTS

| | | |
|---|---|---|
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0035685 A1 | 2/2012 | Saha et al. |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078129 A1 | 3/2012 | Bailin |
| 2012/0078322 A1 | 3/2012 | Dal Molin et al. |
| 2012/0089198 A1 | 4/2012 | Ostroff |
| 2012/0089214 A1 | 4/2012 | Kroll et al. |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109235 A1 | 5/2012 | Sheldon et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232478 A1 | 9/2012 | Haslinger |
| 2012/0232563 A1 | 9/2012 | Williams et al. |
| 2012/0232565 A1 | 9/2012 | Kveen et al. |
| 2012/0245665 A1 | 9/2012 | Friedman et al. |
| 2012/0263218 A1 | 10/2012 | Dal Molin et al. |
| 2012/0277600 A1 | 11/2012 | Greenhut |
| 2012/0277606 A1 | 11/2012 | Ellingson et al. |
| 2012/0277725 A1 | 11/2012 | Kassab et al. |
| 2012/0283587 A1 | 11/2012 | Gosh et al. |
| 2012/0283795 A1 | 11/2012 | Stancer et al. |
| 2012/0283807 A1 | 11/2012 | Deterre et al. |
| 2012/0284003 A1 | 11/2012 | Gosh et al. |
| 2012/0290025 A1 | 11/2012 | Keimel |
| 2012/0296228 A1 | 11/2012 | Zhang et al. |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0013017 A1 | 1/2013 | Mullen et al. |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053906 A1 | 2/2013 | Ghosh et al. |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourg et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116739 A1 | 5/2013 | Brada et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0131750 A1 | 5/2013 | Stadler et al. |
| 2013/0131751 A1 | 5/2013 | Stadler et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197599 A1 | 8/2013 | Sambelashvili et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Walfhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268017 A1 | 10/2013 | Zhang et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0138006 A1 | 11/2013 | Bornzin et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0339570 A1 | 2/2014 | Carroll et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0114173 A1 | 4/2014 | Bar-Tal et al. |
| 2014/0114372 A1 | 4/2014 | Ghosh et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |

(56) References Cited

U.S. PATENT DOCUMENTS

| | | |
|---|---|---|
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0323882 A1 | 10/2014 | Ghosh et al. |
| 2014/0323892 A1 | 10/2014 | Ghosh et al. |
| 2014/0330208 A1 | 11/2014 | Christie et al. |
| 2014/0330287 A1 | 11/2014 | Thompson-Nauman et al. |
| 2014/0330326 A1 | 11/2014 | Thompson-Nauman et al. |
| 2014/0358135 A1 | 12/2014 | Sambelashvili et al. |
| 2014/0371832 A1 | 12/2014 | Ghosh |
| 2014/0371833 A1 | 12/2014 | Ghosh et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Foster et al. |
| 2015/0105836 A1 | 4/2015 | Bonner et al. |
| 2015/0142070 A1 | 5/2015 | Sambelashvili |
| 2015/0148697 A1 | 5/2015 | Burnes et al. |
| 2015/0149096 A1 | 5/2015 | Soykan |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0305695 A1 | 10/2015 | Lahm et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335894 A1 | 11/2015 | Bornzin et al. |
| 2016/0015287 A1 | 1/2016 | Anderson et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0045738 A1 | 2/2016 | Ghosh et al. |
| 2016/0045744 A1 | 2/2016 | Gillberg et al. |
| 2016/0051821 A1 | 2/2016 | Sambelashvili et al. |
| 2016/0059002 A1 | 3/2016 | Grubac et al. |
| 2016/0067486 A1 | 3/2016 | Brown et al. |
| 2016/0067487 A1 | 3/2016 | Demmer et al. |
| 2016/0067490 A1 | 3/2016 | Carney et al. |
| 2016/0110856 A1 | 4/2016 | Hoof et al. |
| 2016/0114161 A1 | 4/2016 | Amblard et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0129239 A1 | 5/2016 | Anderson |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0310733 A1 | 10/2016 | Sheldon et al. |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0056670 A1 | 3/2017 | Sheldon et al. |
| 2017/0182327 A1 | 6/2017 | Liu |
| 2017/0189681 A1 | 7/2017 | Anderson |
| 2017/0209689 A1 | 7/2017 | Chen |
| 2017/0216575 A1 | 8/2017 | Asleson et al. |
| 2017/0246461 A1 | 8/2017 | Ghosh |
| 2017/0304624 A1 | 10/2017 | Friedman et al. |
| 2017/0326369 A1 | 11/2017 | Koop et al. |
| 2017/0340885 A1 | 11/2017 | Sambelashvili |
| 2018/0008829 A1 | 1/2018 | An et al. |
| 2018/0021567 A1 | 1/2018 | An et al. |
| 2018/0021581 A1 | 1/2018 | An et al. |
| 2018/0021582 A1 | 1/2018 | An et al. |
| 2018/0050208 A1 | 2/2018 | Shuros et al. |
| 2018/0078773 A1 | 3/2018 | Thakur et al. |
| 2018/0078779 A1 | 3/2018 | An et al. |
| 2018/0117324 A1 | 5/2018 | Schilling et al. |
| 2018/0140848 A1 | 5/2018 | Stahmann |
| 2018/0178007 A1 | 6/2018 | Shuros et al. |
| 2018/0212451 A1 | 7/2018 | Schmidt et al. |
| 2018/0256904 A1 | 9/2018 | Li et al. |
| 2018/0264262 A1 | 9/2018 | Haasl et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0272121 A1* | 9/2018 | Yankelson ......... A61N 1/37518 |
| 2018/0280686 A1 | 10/2018 | Shuros et al. |
| 2018/0326215 A1 | 11/2018 | Ghosh |
| 2019/0030346 A1 | 1/2019 | Li |
| 2019/0038906 A1 | 2/2019 | Koop et al. |
| 2019/0083779 A1 | 3/2019 | Yang et al. |
| 2019/0083800 A1 | 3/2019 | Yang et al. |
| 2019/0083801 A1 | 3/2019 | Yang et al. |
| 2019/0192860 A1 | 6/2019 | Ghosh et al. |
| 2019/0269926 A1 | 9/2019 | Ghosh |
| 2019/0290909 A1 | 9/2019 | Ghosh |
| 2021/0085986 A1 | 3/2021 | Li et al. |

FOREIGN PATENT DOCUMENTS

| | | |
|---|---|---|
| AU | 2014203793 A1 | 7/2014 |
| CN | 202933393 | 5/2013 |
| EP | 0362611 A1 | 4/1990 |
| EP | 0459 239 A2 | 12/1991 |
| EP | 0 728 497 A2 | 8/1996 |
| EP | 1 541 191 A1 | 6/2005 |
| EP | 1 702 648 A1 | 9/2006 |
| EP | 1 904 166 B1 | 6/2011 |
| EP | 2 452 721 A1 | 5/2012 |
| EP | 2 471 452 A1 | 7/2012 |
| EP | 2 662 113 A2 | 11/2013 |
| EP | 1 703 944 B1 | 7/2015 |
| JP | 2005245215 | 9/2005 |
| WO | WO 95/00202 | 1/1995 |
| WO | WO 96/36134 | 11/1996 |
| WO | WO 97/24981 | 7/1997 |

(56) References Cited

FOREIGN PATENT DOCUMENTS

| | | |
|---|---|---|
| WO | WO 02/22206 A1 | 3/2002 |
| WO | WO 03/092800 A1 | 11/2003 |
| WO | WO 2005/000206 A2 | 1/2005 |
| WO | WO 2005/042089 A1 | 5/2005 |
| WO | WO 2006/086435 A2 | 8/2006 |
| WO | WO 2006/113659 A1 | 10/2006 |
| WO | WO 2007/073435 A1 | 6/2007 |
| WO | WO 2007/075974 A1 | 7/2007 |
| WO | WO 2009/006531 A1 | 1/2009 |
| WO | WO 2018/017226 A1 | 1/2010 |
| WO | WO 2013/080038 A2 | 6/2013 |
| WO | WO 2013/098644 A2 | 7/2013 |
| WO | WO 2015/081221 A1 | 6/2015 |
| WO | WO 2016/011042 A1 | 1/2016 |
| WO | WO 2016/077099 A1 | 5/2016 |
| WO | WO 2016/110856 A1 | 7/2016 |
| WO | WO 2016/171891 A1 | 10/2016 |
| WO | WO 2017/075193 A1 | 5/2017 |
| WO | WO 2018/009569 A1 | 1/2018 |
| WO | WO 2018/017361 A1 | 1/2018 |
| WO | WO 2018/035343 A1 | 2/2018 |
| WO | WO 2018/081519 A1 | 5/2018 |

OTHER PUBLICATIONS

International Search Report and Written Opinion from PCT Application No. PCT/US2020/047802 dated Nov. 19, 2020, 9 pages.

http://www.isrctn.com/ISRCTN47824547, public posting published Aug. 2019.

Abed et al., "Obesity results in progressive atrial structural and electrical remodeling: Implications for atrial fibrillation," *Heart Rhythm Society*, Jan. 2013; 10(1):90-100.

Adragão et al., "Ablation of pulmonary vein foci for the treatment of atrial fibrillation; percutaneous electroanatomical guided approach," *Europace*, Oct. 2002; 4(4):391-9.

Aliot et al., "Arrhythmia detection by dual-chamber implantable cardioverter defibrillators: A review of current algorithms," *Europace*, Jul. 2004; 6(4):273-86.

Amirahmadi et al., "Ventricular Tachycardia Caused by Mesothelial Cyst," *Indian Pacing and Electrophysiology Journal*, 2013; 13(1):43-44.

Ammirabile et al., "Pitx2 confers left morphological, molecular, and functional identity to the sinus venosus myocardium," *Cardiovasc Res.*, Feb. 2012; 93(2):291-301.

Anderson et al., "Left bundle branch block and the evolving role of QRS morphology in selection of patients for cardiac resynchronization", Journal of Interventional Cardio Electrophysiology, vol. 52, No. 3. Aug. 20, 2018, pp. 353-374.

Anfinsen, "Non-pharmacological Treatment of Atrial Fibrillation," *Indian Pacing and Electrophysiology Journal*, Jan. 2002; 2(1):4-14.

Anné et al., "Ablation of post-surgical intra-atrial reentrant Tachycardia," *European Heart Journal*, 2002; 23:169-1616.

Arenal et al., "Dominant frequency differences in atrial fibrillation patients with and without left ventricular systolic dysfunction," *Europace*, Apr. 2009; 11(4):450-457.

Arriagada et al., "Predictors of arrhythmia recurrence in patients with lone atrial fibrillation," *Europace*, Jan. 2008; 10(1):9-14.

Asirvatham et al., "Cardiac Anatomic Considerations in Pediatric Electrophysiology," *Indian Pacing and Electrophysiology Journal*, Apr. 2008; 8(Suppl 1):S75-S91.

Asirvatham et al., "Intramyocardial Pacing and Sensing for the Enhancement of Cardiac Stimulation and Sensing Specificity," *Pacing Clin. Electrophysiol.*, Jun. 2007; 30(6):748-754.

Asirvatham et al., "Letter to the Editor," *J Cardiovasc Electrophysiol.*, Mar. 2010; 21(3): E77.

Balmer et al., "Long-term follow up of children with congenital complete atrioventricular block and the impact of pacemaker therapy," *Europace*, Oct. 2002, 4(4):345-349.

Barold et al., "Conventional and biventricular pacing in patients with first-degree atrioventricular block," *Europace*, Oct. 2012, 14(10):1414-9.

Barold et al., "The effect of hyperkalaemia on cardiac rhythm devices," *Europace*, Apr. 2014; 16(4):467-76.

Bayrak et al., "Added value of transoesophageal echocardiography during transseptal puncture performed by inexperienced operators," *Europace*, May 2012, 14(5):661-5.

Bergau et al., "Measurement of Left Atrial Pressure is a Good Predictor of Freedom From Atrial Fibrillation," *Indian Pacing and Electrophysiology Journal*, Jul. 2014; 14(4):181-93.

Bernstein et al., "The revised NASPE/BPEG generic code for antibradycardia, adaptive-rate, and multisite pacing. North American Society of Pacing and Electrophysiology/British Pacing and Electrophysiology Group," *Pacing Clin Electrophysiol.*, Feb. 2002; 25(2):260-4.

Bito et al., "Early exercise training after myocardial infarction prevents contractile but not electrical remodeling or hypertrophy," *Cardiovascular Research*, Apr. 2010; 86(1):72-81.

Bollmann et al., "Analysis of surface electrocardiograms in atrial fibrillation: techniques, research, and clinical applications," *Europace*, Nov. 2006; 8(11):911-926.

Bortone et al., "Evidence for an incomplete mitral isthmus block after failed ablation of a left postero-inferior concealed accessory pathway," *Europace*, Jun. 2006; 8(6):434-7.

Boulos et al., "Electroanatomical mapping and radiofrequency ablation of an accessory pathway associated with a large aneurysm of the coronary sinus," *Europace*, Nov. 2004; 6(6):608-12.

Brembilla-Perrot et al., "Incidence and prognostic significance of spontaneous and inducible antidromic tachycardia," *Europace*, Jun. 2013; 15(6):871-876.

Buber et al., "Morphological features of the P-waves at surface electrocardiogram as surrogate to mechanical function of the left atrium following a successful modified maze procedure," *Europace*, Apr. 2014; 16(4):578-86.

Burashnikov et al., "Late-phase 3 EAD. A unique mechanism contributing to initiation of atrial fibrillation," *Pacing Clin Electrophysiol.*, Mar. 2006, 29(3):290-5.

Burashnikov et al., "Atrial-selective inhibition of sodium-channel current by Wenxin Keli is effective in suppressing atrial fibrillation," *Heart Rhythm*, Jan. 2012, 9(1):125-31.

Calvo et al., "Efficacy of circumferential pulmonary vein ablation of atrial fibrillation in endurance athletes," *Europace*, Jan. 2010; 12(1):30-6.

Can et al., ""Atrial torsades de pointes" Induced by Low-Energy Shock From Implantable-Cardioverter Defibrillator," *Indian Pacing and Electrophysiology Journal*, Sep. 2013; 13(5):194-199.

Carroz et al., "Pseudo-pacemaker syndrome in a young woman with first-degree atrio-ventricular block," *Europace*, Apr. 2010; 12(4):594-596.

Catanchin et al., "Wolff-Parkinson-White syndrome with an unroofed coronary sinus without persistent left superior vena cava treated with catheter cryoablation," *Indian Pacing and Electrophysiology Journal*, Aug. 2008; 8(3):227-233.

Cazeau et al., "Cardiac resynchronization therapy," *Europace*, Sep. 2004; 5 Suppl 1:S42-8.

Cerqueira et al., "Standardized myocardial segmentation and nomenclature for tomographic imaging of the heart. A statement for healthcare professionals from the Cardiac Imaging Committee of the Council on Clinical Cardiology of the American Heart Association," *Circulation*, Jan. 29, 2002; 105(4):539-42.

Chandra et al., "Evaluation of KCB-328, a new IKr blocking anti arrhythmic agent in pacing induced canine atrial fibrillation," *Europace*, Sep. 2004; 6(5):384-91.

Chang et al., "Electrophysiological characteristics and catheter ablation in patients with paroxysmal supraventricular tachycardia and paroxysmal atrial fibrillation," *J Cardiovasc Electrophysiol.*, Apr. 2008; 19(4):367-73.

Charron et al., "A familial form of conduction defect related to a mutation in the PRKAG2 gene," *Europace*, Aug. 2007; 9(8):597-600.

(56) References Cited

OTHER PUBLICATIONS

Chou et al., "Effects of SEA0400 on Arrhythmogenicity in a Langendorff-Perfused 1-Month Myocardial Infarction Rabbit Model," *Pacing Clin Electrophysiol.*, May 2013; 36(5):596-606.

Ciploetta et al., "Posterior Coronary Vein as the Substrate for an Epicardial Accessory Pathway," *Indian Pacing and Electrophysiology Journal*, Aug. 2013; 13(4):142-7.

Climent et al., "Effects of endocardial microwave energy ablation," *Indian Pacing and Electrophysiology Journal*, Jul. 2005; 5(3):233-43.

Comtois et al., "Of circles and spirals: bridging the gap between the leading circle and spiral wave concepts of cardiac reentry," *Europace*, Sep. 2005; 7 Suppl 2:10-20.

Crick et al., "Anatomy of the pig heart: comparisons with normal human cardiac structure," *J. Anat.*, 1998, 193:105-119.

Daoulah et al., "Unintended Harm and Benefit of the Implantable Defibrillator in an Unfortunate 19-Year-Old Male: Featuring a Sequence of Rare Life-threatening Complications of Cardiac Procedures," *Indian Pacing and Electrophysiology Journal*, Aug. 2013; 13(4):151-6.

De Mattia et al., "Paroxysmal atrial fibrillation triggered by a monomorphic ventricular couplet in a patient with acute coronary syndrome," *Indian Pacing and Electrophysiology Journal*, Jan. 2012; 12(1):19-23.

DeSimone et al., "New approach to cardiac resynchronization therapy: CRT without left ventricular lead," Apr. 25, 2014, 2 pages.

De Sisti et al., "Electrophysiological determinants of atrial fibrillation in sinus node dysfunction despite atrial pacing," *Europace*, Oct. 2000; 2(4):304-11.

De Voogt et al., "Electrical characteristics of low atrial septum pacing compared with right atrial appendage pacing," *Europace*, Jan. 2005; 7(1):60-6.

De Voogt et al., "A technique of lead insertion for low atrial septal pacing," *Pacing Clin Electrophysiol.*, Jul. 2005, 28(7):639-46.

Dizon et al. "Real-time stroke volume measurements for the optimization of cardiac resynchronization therapy parameters," *Europace*, Sep. 2010; 12(9):1270-1274.

Duckett et al., "Relationship between endocardial activation sequences defined by high-density mapping to early septal contraction (septal flash) in patients with left bundle branch block undergoing cardiac resynchronization therapy," *Europace*, Jan. 2012; 14(1):99-106.

Eksik et al., "Influence of atrioventricular nodal reentrant tachycardia ablation on right to left inter-atrial conduction," *Indian Pacing and Electrophysiology Journal*, Oct. 2005; 5(4):279-88.

Fiala et al., "Left Atrial Voltage during Atrial Fibrillation in Paroxysmal and Persistent Atrial Fibrillation Patients," *PACE*, May 2010; 33(5):541-548.

Fragakis et al., "Acute beta-adrenoceptor blockade improves efficacy of ibutilide in conversion of atrial fibrillation with a rapid ventricular rate," *Europace*, Jan. 2009; 11(1):70-4.

Frogoudaki et al., "Pacing for adult patients with left atrial isomerism: efficacy and technical considerations," *Europace*, Apr. 2003; 5(2):189-193.

Ganapathy et al., "Implantable Device to Monitor Cardiac Activity with Sternal Wires," *Pacing Clin. Electrophysiol.*, Dec. 2014; Epub Aug. 24, 2014; 37(12):1630-40.

Geddes, "Accuracy limitations of chronaxie values," *IEEE Trans Biomed Eng.*, Jan. 2004; 51(1):176-81.

Gertz et al., "The impact of mitral regurgitation on patients undergoing catheter ablation of atrial fibrillation," *Europace*, Aug. 2011; 13(8):1127-32.

Girmatsion et al., "Changes in microRNA-1 expression and IK 1 up-regulation in human atrial fibrillation," *Heart Rhythm*, Dec. 2009; 6(12):1802-9.

Goette et al., "Acute atrial tachyarrhythmia induces angiotensin II type 1 receptor-mediated oxidative stress and microvascular flow abnormalities in the ventricles," *European Heart Journal*, Jun. 2009; 30(11):1411-20.

Goette et al., "Electrophysiological effects of angiotensin II. Part I: signal transduction and basic electrophysiological mechanisms," *Europace*, Feb. 2008; 10(2):238-41.

Gómez et al., "Nitric oxide inhibits Kv4.3 and human cardiac transient outward potassium current (Ito1)," *Cardiovasc Res.*, Dec. 2008; 80(3):375-84.

Gros et al., "Connexin 30 is expressed in the mouse sino-atrial node and modulates heart rate," *Cardiovascular Research*, Jan. 2010; 85(1):45-55.

Guenther et al., "Substernal Lead Implantation: A Novel Option to Manage OFT Failure in S-ICD patients," *Clinical Research Cardiology*, Feb. 2015; Epub Oct. 2, 2014; 104(2):189-91.

Guillem et al., "Noninvasive mapping of human atrial fibrillation," *J Cardiovasc Electrophysiol.*, May 2009; 20(5):507-513.

Hachisuka et al., "Development and Performance Analysis of an Intra-Body Communication Device," The $12^{th}$ International Conference on Solid State Sensors, Actuators and Microsystems, vol. 4A1.3, pp. 1722-1725, 2003.

Hakacova et al., "Septal atrial pacing for the prevention of atrial fibrillation," *Europace*, 2007; 9:1124-1128.

Hasan et al., "Safety, efficacy, and performance of implanted recycled cardiac rhythm management (CRM) devices in underprivileged patients," *Pacing Clin Eiectrophysiol.*, Jun. 2011; 34(6):653-8.

Hawkins, "Epicardial Wireless Pacemaker for Improved Left Ventricular Reynchronization (Conceptual Design)", Dec. 2010, A Thesis presented to the Faculty of California Polytechnic State University, San Luis Obispo, 57 pp.

He et al., "Three-dimensional cardiac electrical imaging from intracavity recordings," *IEEE Trans Biomed Eng.*, Aug. 2007; 54(8):1454-60.

Heist et al., "Direct visualization of epicardial structures and ablation utilizing a visually guided laser balloon catheter: preliminary findings," *J Cardiovasc Eiectrophysiol.*, Jul. 2011; 22(7):808-12.

Henz et al., "Synchronous Ventricular Pacing without Crossing the Tricuspid Valve or Entering the Coronary Sinus—Preliminary Results," *J Cardiovasc Eiectrophysiol.*, Dec. 2009; 20(12):1391-1397.

Hiippala et al., "Automatic Atrial Threshold Measurement and Adjustment in Pediatric Patients," *Pacing Clin Eiectrophysiol.*, Mar. 2010; 33(3):309-13.

Ho, "Letter to the Editor" *J Cardiovasc Eiectrophysiol.*, Mar. 2010; 21(3): E76.

Höijer et al., "Improved cardiac function and quality of life following upgrade to dual chamber pacing after long-term ventricular stimulation," *European Heart Journal*, Mar. 2002; 23(6):490-497.

Huang et al., "A Novel Pacing Strategy With Low and Stable Output: Pacing the Left Bundle Branch Immediately Beyond the Conduction Block," *Can J Cardiol.*, Dec. 2007; Epub Sep. 22, 2017; 33(12):1736.e1-1736.e.

Inter-Office Memo, Model 6426-85 Canine Feasibility AV Septal 8 mm Screw-In Right Single Pass DDD Lead Final Report (AR # 0120A0207).

Ishigaki et al., "Prevention of immediate recurrence of atrial fibrillation with low-dose landiolol after radiofrequency catheter ablation," *Journal of Arrhythmia*, Oct. 2015; 31(5):279-285.

Israel, "The role of pacing mode in the development of atrial fibrillation," *Europace*, Feb. 2006; 8(2):89-95.

Janion et al., "Dispersion of P wave duration and P wave vector in patients with atrial septal aneurysm," *Europace*, Jul. 2007; 9(7):471-4.

Kabra et al., "Recent Trends in Imaging for Atrial Fibrillation Ablation," *Indian Pacing and Electrophysiology Journal*, 2010; 10(5):215-227.

Kalbfleisch et al., "Catheter Ablation with Radiofrequency Energy: Biophysical Aspects and Clinical Applications," *Journal of Cardiovascular Electrophysiology*, Oct. 2008; 3(2):173-186.

Katritsis et al., "Classification and differential diagnosis of atrioventricular nodal re-entrant tachycardia," *Europace*, Jan. 2006; 8(1):29-36.

Katritsis et al., "Anatomically left-sided septal slow pathway ablation in dextrocardia and situs inversus totalis," *Europace*, Aug. 2008; 10(8):1004-5.

(56) References Cited

OTHER PUBLICATIONS

Khairy et al., "Cardiac Arrhythmias In Congenital Heart Diseases," *Indian Pacing and Electrophysiology Journal*, Nov.-Dec. 2009; 9(6):299-317.

Kimmel et al., "Single-site ventricular and biventricular pacing: investigation of latest depolarization strategy," *Europace*, Dec. 2007, 9(12):1163-1170.

Knackstedt et al., "Electro-anatomic mapping systems in arrhythmias," *Europace*, Nov. 2008; 10 Suppl 3:iii28-iii34.

Kobayashi et al., "Successful Ablation of Antero-septal Accessory Pathway in the Non-Coronary Cusp in a Child," *Indian Pacing and Electrophysiology Journal*, 2012; 12(3):124-130.

Kojodjojo et al., "4:2:1 conduction of an AF initiating trigger," *Indian Pacing and Electrophysiology Journal*, Nov. 2015; 15(5):255-8.

Kołodzińska et al., "Differences in encapsulating lead tissue in patients who underwent transvenous lead removal," *Europace*, Jul. 2012; 14(7):994-1001.

Konecny et al., "Synchronous intra-myocardial ventricular pacing without crossing the tricuspid valve or entering the coronary sinus," *Cardiovascular Revascularization Medicine*, 2013, 14:137-138.

Kriatselis et al., "Ectopic atrial tachycardias with early activation at His site: radiofrequency ablation through a retrograde approach," *Europace*, Jun. 2008; 10(6):698-704.

Lalu et al., "Ischaemia-reperfusion injury activates matrix metalloproteinases in the human heart," *Eur Heart J.*, Jan. 2005; 26(1):27-35.

Laske et al., "Excitation of the Intrinsic Conduction System Through His and Interventricular Septal Pacing," *Pacing Clin. Electrophysiol.*, Apr. 2006; 29(4):397-405.

Leclercq, "Problems and troubleshooting in regular follow-up of patients with cardiac resynchronization therapy," *Europace*, Nov. 2009; 11 Suppl 5:v66-71.

Lee et al., "An unusual atrial tachycardia in a patient with Friedreich ataxia," *Europace*, Nov. 2011, 13(11):1660-1.

Lee et al., "Blunted Proarrhythmic Effect of Nicorandil in a Langendorff-Perfused Phase-2 Myocardial Infarction Rabbit Model," *Pacing Clin Electrophysiol.*, Feb. 2013; 36(2):142-51.

Lemay et al., "Spatial dynamics of atrial activity assessed by the vectorcardiogram: from sinus rhythm to atrial fibrillation," *Europace*, Nov. 2007; 9 Suppl 6:vi109-18.

Levy et al., "Does the mechanism of action of biatrial pacing for atrial fibrillation involve changes in cardiac haemodynamics? Assessment by Doppler echocardiography and natriuretic peptide measurements," *Europace*, Apr. 2000; 2(2):127-35.

Lewalter et al., "Comparison of spontaneous atrial fibrillation electrogram potentials to the P wave electrogram amplitude in dual chamber pacing with unipolar atrial sensing," *Europace*, Apr. 2000; 2(2):136-40.

Liakopoulos et al., "Sequential deformation and physiological considerations in unipolar right and left ventricular pacing," *European Journal of Cardio-thoracic Surgery*, Apr. 1, 2006; 29S1:S188-197.

Lian et al., "Computer modeling of ventricular rhythm during atrial fibrillation and ventricular pacing," *IEEE Transactions on Biomedical Engineering*, Aug. 2006; 53(8):1512-1520.

Lim et al., "Right ventricular lead implantation facilitated by a guiding sheath in a patient with severe chamber dilatation with tricuspid regurgitation," *Indian Pacing and Electrophysiology Journal*, Sep. 2011; 11(5):156-8.

Lim et al., "Coupled pacing improves left ventricular function during simulated atrial fibrillation without mechanical dyssynchrony," *Europace*, Mar. 2010; 12(3):430-6.

Lou et al., "Tachy-brady arrhythmias: The critical role of adenosine-induced sinoatrial conduction block in post-tachycardia pauses," *Heart Rhythm.*, Jan. 2013; 10(1):110-8.

Lutomsky et al., "Catheter ablation of paroxysmal atrial fibrillation improves cardiac function: a prospective study on the impact of atrial fibrillation ablation on left ventricular function assessed by magnetic resonance imaging," *Europace*, May 2008; 10(5):593-9.

Macedo et al., "Septal accessory pathway: anatomy, causes for difficulty, and an approach to ablation," *Indian Pacing and Electrophysiology Journal*, Jul. 2010; 10(7):292-309.

Mafi-Rad et al., "Feasibility and Acute Hemodynamic Effect of Left Ventricular Septal Pacing by Transvenous Approach Through the Interventricular Septum," *Circ Arrhythm Electrophysoil.*, Mar. 2016; 9(3):e003344.

Mani et al., "Dual Atrioventricular Nodal Pathways Physiology: A Review of Relevant Anatomy, Electrophysiology, and Electrocardiographic Manifestations," *Indian Pacing and Electrophysiology Journal*, Jan. 2014; 14(1):12-25.

Manios et al., "Effects of successful cardioversion of persistent atrial fibrillation on right ventricular refractoriness and repolarization," *Europace*, Jan. 2005; 7(1):34-9.

Manolis et al., "Prevention of atrial fibrillation by inter-atrial septum pacing guided by electrophysiological testing, in patients with delayed interatrial conduction," *Europace*, Apr. 2002; 4(2):165-174.

Marino et al., "Inappropriate mode switching clarified by using a chest radiograph," *Journal of Arrhythmia*, Aug. 2015; 31(4):246-248.

Markowitz et al., "Time course and predictors of autonomic dysfunction after ablation of the slow atrioventricular nodal pathway," *Pacing Clin Electrophysiol.*, Dec. 2004; 27(12):1638-43.

Marshall et al., "The effects of temperature on cardiac pacing thresholds," *Pacing Clin Electrophysiol.*, Jul. 2010; 33(7):826-833.

McSharry et al., "A Dynamical Model for Generating Synthetic Electrocardiogram Signals," *IEEE Transactions on Biomedical Engineering*, Mar. 2003; 50(3):289-294.

Meijler et al., "Scaling of Atrioventricular Transmission in Mammalian Species: An Evolutionary Riddle!," *Journal of Cfardiovascular Electrophysiology*, Aug. 2002; 13(8):826-830.

Meiltz et al., "Permanent form of junctional reciprocating tachycardia in adults: peculiar features and results of radiofrequency catheter ablation," *Europace*, Jan. 2006; 8(1):21-8.

Mellin et al., "Transient reduction in myocardial free oxygen radical levels is involved in the improved cardiac function and structure after long-term allopurinol treatment initiated in established chronic heart failure," *Eur Heart J.*, Aug. 2005; 26(15):1544-50.

Mestan et al., "The influence of fluid and diuretic administration on the index of atrial contribution in sequentially paced patients," *Europace*, Apr. 2006; 8(4):273-8.

Metin et al., "Assessment of the P Wave Dispersion and Duration in Elite Women Basketball Players," *Indian Pacing and Electrophysiology Journal*, 2010; 10(1):11-20.

Mills et al., "Left Ventricular Septal and Left Ventricular Apical Pacing Chronically Maintain Cardiac Contractile Coordination, Pump Function and Efficiency," *Circ Arrhythm. Electrophysoil.*, Oct. 2009; 2(5):571-579.

Mitchell et al., "How do atrial pacing algorithms prevent atrial arrhythmias?" *Europace*, Jul. 2004; 6(4):351-62.

Mirzoyev et al., "Embryology of the Conduction System for the Electrophysiologist," *Indian Pacing and Electrophysiology Journal*, 2010; 10(8):329-338.

Modre et al., "Noninvasive Myocardial Activation Time Imaging: A Novel Inverse Algorithm Applied to Clinical ECG Mapping Data," *IEE Transactions on Biomedical Engineering*, Oct. 2002; 49(10):1153-1161.

Montgomery et al., "Measurement of diffuse ventricular fibrosis with myocardial T1 in patients with atrial fibrillation," *J Arrhythm.*, Feb. 2016; 32(1):51-6.

Mulpuru et al., "Synchronous ventricular pacing with direct capture of the atrioventricular conduction system: Functional anatomy, terminology, and challenges," *Heart Rhythm*, Nov. 2016; Epub Aug. 3, 2016; 13(11):2237-2246.

Musa et al., "Inhibition of Platelet-Derived Growth Factor-AB Signaling Prevents Electromechanical Remodeling of Adult Atrial Myocytes that Contact Myofibroblasts," *Heart Rhythm*, Jul. 2013; 10(7):1044-1051.

Nagy et al., "Wnt-11 signalling controls ventricular myocardium development by patterning N-cadherin and β-catenin expression," *Cardiovascular Research*, Jan. 2010; 85(1):100-9.

(56) References Cited

OTHER PUBLICATIONS

Namboodiri et al., "Electrophysiological features of atrial flutter in cardiac sarcoidosis: a report of two cases," *Indian Pacing and Electrophysiology Journal*, Nov. 2012; 12(6):284-9.
Nanthakumar et al., "Assessment of accessory pathway and atrial refractoriness by transesophageal and intracardiac atrial stimulation: An analysis of methodological agreement," *Europace*, Jan. 1999; 1(1):55-62.
Neto et al., "Temporary atrial pacing in the prevention of postoperative atrial fibrillation," *Pacing Clin Electrophysiol.*, Jan. 2007; 30(Suppl 1):S79-83.
Nishijima et al., "Tetrahydrobiopterin depletion and NOS2 uncoupling contribute to heart failure-induced alterations in atrial electrophysiology," *Cardiovasc Res.*, Jul. 2011; 91(1):71-9.
Niwano et al., "Effect of oral L-type calcium channel blocker on repetitive paroxysmal atrial fibrillation: spectral analysis of fibrillation waves in the Holter monitoring," *Europace*, Dec. 2007; 9(12):1209-1215.
Okumura et al., "Effects of a high-fat diet on the electrical properties of porcine atria," *Journal of Arrhythmia*, Dec. 2015; 31(6):352-358.
Olesen et al., "Mutations in sodium channel βsubunit SCN3B are associated with early-onset lone atrial fibrillation," *Cardiovascular Research*, Mar. 2011; 89(4):786-93.
Ozmen et al., "P wave dispersion is increased in pulmonary stenosis," *Indian Pacing and Electrophysiology Journal*, Jan. 2006; 6(1):25-30.
Packer et al., "New generation of electro-anatomic mapping: Full intracardiac image integration," *Europace*, Nov. 2008; 10 Suppl 3:iii35-41.
Page et al., "Ischemic ventricular tachycardia presenting as a narrow complex tachycardia," *Indian Pacing and Electrophysiology Journal*, Jul. 2014; 14(4):203-210.
Pakarinen et al., "Pre-implant determinants of adequate long-term function of single lead VDD pacemakers," *Europace*, Apr. 2002; 4:137-141.
Patel et al., "Atrial Fibrillation after Cardiac Surgery: Where are we now?" *Indian Pacing and Electrophysiology Journal*, Oct.-Dec. 2008; 8(4):281-291.
Patel et al., "Successful ablation of a left-sided accessory pathway in a patient with coronary sinus atresia and arteriovenous fistula: clinical and developmental insights," *Indian Pacing and Electrophysiology Journal*, Mar. 2011; 11(2):43-49.
Peschar et al., "Left Ventricular Septal and Apex Pacing for Optimal Pump Function in Canine Hearts," *J Am Coll Cardiol.*, Apr. 2, 2003; 41(7):1218-1226.
Physiological Research Laboratories, Final Report for an Acute Study for Model 6426-85 AV Septal Leads, Feb. 1996.
Porciani et al., "Interatrial septum pacing avoids the adverse effect of interatrial delay in biventricular pacing: an echo-Doppler evaluation," *Europace*, Jul. 2002; 4(3):317-324.
Potse et al., "A Comparison of Monodomain and Bidomain Reaction-Diffusion Models for Action Potential Propagation in the Human Heart," *IEEE Transactions on Biomedical Engineering*, Dec. 2006; 53(12 Pt 1):2425-35.
Prystowsky et al., "Case studies with the experts: management decisions in atrial fibrillation," *J Cardiovasc Electrophysiol.*, Feb. 2008; 19(Suppl. 1):S1-12.
Prystowsky, "The history of atrial fibrillation: the last 100 years," *J Cardiovasc Electrophysiol*, Jun. 2008; 19(6):575-582.
Pytkowski et al., "Paroxysmal atrial fibrillation is associated with increased intra-atrial conduction delay," *Europace*, Dec. 2008; 10(12):1415-20.
Qu et al., "Dynamics and cardiac arrhythmias," *J Cardiovasc Electrophysiol.*, Sep. 2006; 17(9):1042-9.
Ravens et al., "Role of potassium currents in cardiac arrhythmias," *Europace*, Oct. 2008; 10(10):1133-7.
Ricci et al., Efficacy of a dual chamber defibrillator with atrial anti tachycardia functions in treating spontaneous atrial tachyarrhythmias in patients with lifethreatening ventricular tachyarrhythmias, *European Heart Journal*, Sep. 2002; 23(18):1471-9.
Roberts-Thomson et al., "Focal atrial tachycardia II: management," *Pacing Clin Electrophysiol.*, Jul. 2006; 29(7):769-78.
Rossi et al., "Endocardial vagal atrioventricular node stimulation in humans: reproducibility on 18-month follow-up," *Europace*, Dec. 2010; 12(12):1719-24.
Rouzet et al., "Contraction delay of the RV outflow tract in patients with Brugada syndrome is dependent on the spontaneous ST-segment elevation pattern," *Heart Rhythm*, Dec. 2011; 8(12):1905-12.
Russo et al., "Atrial Fibrillation and Beta Thalassemia Major: The Predictive Role of the 12-lead Electrocardiogram Analysis," *Indian Pacing and Electrophysiology Journal*, May 2014; 14(3):121-32.
Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, Feb. 2010, 21(2): 219-22.
Sairaku et al., "Prediction of sinus node dysfunction in patients with persistent atrial flutter using the flutter cycle length," *Europace*, Mar. 2012; 14(3):380-7.
Santini et al., "Immediate and long-term atrial sensing stability in single-lead VDD pacing depends on right atrial dimensions," *Europace*, Oct. 2001; 3(4):324-31.
Saremi et al., "Cardiac Conduction System: Delineation of Anatomic Landmarks With Multidetector CT," *Indian Pacing and Electrophysiology*, Journal, Nov. 2009; 9(6):318-33.
Savelieva et al., "Anti-arrhythmic drug therapy for atrial fibrillation: current anti-arrhythmic drugs, investigational agents, and innovative approaches," *Europace*, Jun. 2008; 10(6):647-665.
Schmidt et al., "Navigated DENSE strain imaging for post-radiofrequency ablation lesion assessment in the swine left atria," *Europace*, Jan. 2014; 16(1):133-41.
Schoonderwoerd et al., "Rapid Pacing Results in Changes in Atrial but not in Ventricular Refractoriness," *Pacing Clin Electrophysiol.*, Mar. 2002; 25(3):287-90.
Schoonderwoerd et al., "Atrial natriuretic peptides during experimental atrial tachycardia: role of developing tachycardiomyopathy," *J Cardiovasc Electrophysiol.*, Aug. 2004; 15(8):927-32.
Schoonderwoerd et al., "Atrial ultrastructural changes during experimental atrial tachycardia depend on high ventricular rate," *J Cardiovasc Electrophysiol.*, Oct. 2004; 15(10):1167-74.
Sedmera, "Function and form in the developing cardiovascular system," *Cardiovasc Res.*, Jul. 2011; 91(2):252-9.
Severi et al., "Alterations of atrial electrophysiology induced by electrolyte variations: combined computational and P-wave analysis," *Europace*, Jun. 2010; 12(6):842-9.
Seyedi et al., "A Survey on Intrabody Communications for Body Area Network Application," IEEE Transactions on Biomedical Engineering, vol. 60(8): 2067-2079, 2013.
Shah et al., "Stable atrial sensing on long-term follow up of VDD pacemakers," *Indian Pacing and Electrophysiology Journal*, Oct. 2006; 6(4):189-93.
Shenthar et al., "Permanent pacemaker implantation in a patient with situs solitus, dextrocardia, and corrected transposition of the great arteries using a novel angiographic technique," *Journal of Arrhythmia*, Apr. 2014; 30(2):134-138.
Shenthar et al., "Transvenous permanent pacemaker implantation in dextrocardia: technique, challenges, outcome, and a brief review of literature," *Europace*, Sep. 2014; 16(9):1327-33.
Shirayama, "Role of atrial fibrillation threshold evaluation on guiding treatment," *Indian Pacing and Electrophysiology Journal*, Oct. 2003; 3(4):224-230.
Sperzel et al., "Intraoperative Characterization of Interventricular Mechanical Dyssynchrony Using Electroanatomic Mapping System—A Feasibility Study," Journal of Interventional Cardiac Electrophysiology, Nov. 2012, 35(2): 189-96.
Spickler et al., "Totally Self-Contained Intracardiac Pacemaker," Journal of Electrocardiology, vol. 3(3&4): 324-331, 1970.
Sreeram et al., "Indications for Electrophysiology Study in children," *Indian Pacing and Electrophysiology Journal*, Apr.-Jun. 2008; 8(Suppl. 1):S36-S54.
Stockburger et al., "Optimization of cardiac resynchronization guided by Doppler echocardiography: haemodynamic improvement

(56) References Cited

OTHER PUBLICATIONS and intraindividual variability with different pacing configurations and atrioventricular delays," *Europace*, Oct. 2006; 8(10):881-6.

Stroobandt et al., "Prediction of Wenckebach Behavior and Block Response in DDD Pacemakers," *Pacing Clin Electrophysiol.*, Jun. 2006; 9(6):1040-6.

Suenari et al., "Idiopathic left ventricular tachycardia with dual electrocardiogram morphologies in a single patient," *Europace*, Apr. 2010; 12(4):592-4.

Sweeney et al., "Analysis of Ventricular Activation Using Surface Electrocardiography to Predict Left Ventricular Reverse Volumetric Remodeling During Cardiac Resynchronization Therapy," *Circulation*, Feb. 9, 2010, 121(5): 626-34.

Tan et al., "Electrocardiographic evidence of ventricular repolarization remodelling during atrial fibrillation," *Europace*, Jan. 2008; 10(1):99-104.

Taramasco et al., "Internal low-energy cardioversion: a therapeutic option for restoring sinus rhythm in chronic atrial fibrillation after failure of external cardioversion," *Europace*, Jul. 1999; 1(3):179-82.

Testa et al., "Rate-control or rhythm-control: where do we stand?" *Indian Pacing and Electrophysiology Journal*, Oct. 2005; 5(4):296-304.

Thejus et al., "N-terminal Pro-Brain Natriuretic Peptide and Atrial Fibrillation," *Indian Pacing and Electrophysiology Journal*, Jan. 2009; 9(1):1-4.

Thornton et al., "Magnetic Assisted Navigation in Electrophysiology and Cardiac Resynchronisation: A Review," *Indian Pacing and Electrophysiology Journal*, Oct. 2006; 6(4):202-13.

Tilz et al., "In vivo left-ventricular contact force analysis: comparison of antegrade transseptal with retrograde transaortic mapping strategies and correlation of impedance and electrical amplitude with contact force," *Europace*, Sep. 2014; 16(9):1387-95.

Tomaske et al., "Do daily threshold trend fluctuations of epicardial leads correlate with pacing and sensing characteristics in paediatric patients?" *Europace*, Aug. 2007; 9(8):662-668.

Tomioka et al., "The effect of ventricular sequential contraction on helical heart during pacing: high septal pacing versus biventricular pacing," *European Journal of Cardio-thoracic Surgery*, Apr. 1, 2006; 29S1:S198-206.

Tournoux et al., "A 'Regularly Irregular' tachycardia: What is the diagnosis?" *Europace*, Dec. 2008; 10(12):1445-6.

Traykov et al., "Electrogram analysis at the His bundle region and the proximal coronary sinus as a tool to predict left atrial origin of focal atrial tachycardias," *Europace*, Jul. 2011; 13(7):1022-7.

Trudel et al., "Simulation of QRST integral maps with a membrane-based computer heart model employing parallel processing," *IEEE Trans Biomed Eng.*, Aug. 2004; 51(8):1319-29.

Tse et al., "Cardiac dynamics: Alternans and arrhythmogenesis," *Journal of Arrhythmia*, Oct. 2016; 32(5):411-417.

Tse, "Mechanisms of cardiac arrhythmias," *Journal of Arrhythmia*, Apr. 2016; 32(2):75-81.

Ueda et al., "Outcomes of single- or dual-chamber implantable cardioverter defibrillator systems in Japanese patients," *Journal of Arrhythmia*, Apr. 2016; 32(2):89-94.

Van Dam et al., "Volume conductor effects involved in the genesis of the P wave," *Europace*, Sep. 2005; 7 Suppl 2:30-8.

Van den Berg et al., "Depletion of atrial natriuretic peptide during longstanding atrial fibrillation," *Europace*, Sep. 2004; 6(5):433-7.

Van Deursen, et al., "Vectorcardiography as a Tool for Easy Optimization of Cardiac Resynchronization Therapy in Canine LBBB Hearts," Circulation Arrhythmia and Electrophysiology, Jun. 1, 2012, 5(3): 544-52.

Van Opstal et al., "Paradoxical increase of stimulus to atrium interval despite His-bundle capture during para-Hisian pacing," *Europace*, Dec. 2009; 11(12):1702-4.

Veenhuyzen et al., "Diagnostic pacing maneuvers for supraventricular tachycardia: part 1," *Pacing Clin Electrophysiol.*, Jun. 2011; 34(6):767-82.

Veenhuyzen et al., "Diagnostic pacing maneuvers for supraventricular tachycardias: part 2," *Pacing Clin Electrophysiol.*, Jun. 2012; 35(6):757-69.

Veenhuyzen et al., "Principles of Entrainment: Diagnostic Utility for Supraventricular Tachycardia," *Indian Pacing and Electrophysiology Journal*, 2008; 8(1):51-65.

Verbrugge et al., "Revisiting diastolic filling time as mechanistic insight for response to cardiac resynchronization therapy," *Europace*, Dec. 2013; 15(12):1747-56.

Verrier et al., "Mechanisms of ranolazine's dual protection against atrial and ventricular fibrillation," *Europace*, Mar. 2013; 15(3):317-324.

Verrijcken et al., "Pacemaker-mediated tachycardia with varying cycle length: what is the mechanism?" *Europace*, Oct. 2009; 11(10):1400-2.

Villani et al., "Reproducibility of internal atrial defibrillation threshold in paroxysmal and persistent atrial fibrillation," *Europace*, Jul. 2004; 6(4):267-72.

Violi et al., "Antioxidants for prevention of atrial fibrillation: a potentially useful future therapeutic approach? A review of the literature and meta-analysis," *Europace*, Aug. 2014; 16(8):1107-1116.

Weber et al., "Adenosine sensitive focal atrial tachycardia originating from the noncoronary aortic cusp," *Europace*, Jun. 2009; 11(6):823-6.

Weber et al., "Open-irrigated laser catheter ablation: relationship between the level of energy, myocardial thickness, and collateral damages in a dog model," *Europace*, Jan. 2014; 16(1):142-8.

Wegmoller, "Intra-Body Communication for Biomedical Sensor Networks," Diss. ETH, No. 17323, 1-173, 2007.

Wei et al., "Comparative simulation of excitation and body surface electrocardiogram with isotropic and anisotropic computer heart models," *IEEE Trans Biomed Eng.*, Apr. 1995; 42(4):343-57.

Weijs et al., "Clinical and echocardiographic correlates of intra-atrial conduction delay," *Europace*, Dec. 2011; 13(12):1681-7.

Weiss et al., "The influence of fibre orientation, extracted from different segments of the human left ventricle, on the activation and repolarization sequence: a simulation study," *Europace*, Nov. 2007; 9(Suppl. 6):vi96-vi104.

Wetzel et al., "A stepwise mapping approach for localization and ablation of ectopic right, left, and septal atrial foci using electroanatomic mapping," *European Heart Journal*, Sep. 2002; 23(17):1387-1393.

Wlodarska et al., "Thromboembolic complications in patients with arrhythmogenic right ventricular dysplasia/cardiomyopathy," *Europace*, Aug. 2006; 8(8):596-600.

Wong et al., "A review of mitral isthmus ablation," *Indian Pacing and Electrophysiology Journal*, 2012; 12(4):152-170.

Wu et al., "Acute and long-term outcome after catheter ablation of supraventricular tachycardia in patients after the Mustard or Senning operation for D-transposition of the great arteries," *Europace*, Jun. 2013; 15(6):886-91.

Xia et al., "Asymmetric dimethylarginine concentration and early recurrence of atrial fibrillation after electrical cardioversion," *Pacing Clin Electrophysiol.*, Aug. 2008; 31(8):1036-40.

Yamazaki et al., "Acute Regional Left Atrial Ischemia Causes Acceleration of Atrial Drivers during Atrial Fibrillation," *Heart Rhythm*, Jun. 2013; 10(6):901-9.

Yang et al., "Focal atrial tachycardia originating from the distal portion of the left atrial appendage: Characteristics and long-term outcomes of radiofrequency ablation," *Europace*, Feb. 2012; 14(2):254-60.

Yiginer et al., "Advanced Age, Female Gender and Delay in Pacemaker Implantation May Cause TdP in Patients With Complete Atrioventricular Block," *Indian Pacing and Electrophysiology Journal*, Oct. 2010; 10(10):454-63.

Yoon et al., "Measurement of thoracic current flow in pigs for the study of defibrillation and cardioversion," *IEEE Transactions on Biomedical Engineering*, Oct. 2003; 50(10):1167-1773.

Yuan et al., "Recording monophasic action potentials using a platinum-electrode ablation catheter," *Europace*, Oct. 2000; 2(4):312-9.

(56) References Cited

OTHER PUBLICATIONS

Yusuf et al., "5-Hydroxytryptamine and Atrial Fibrillation: How Significant is This Piece in the Puzzle?" *J Cardiovasc Electrophysiol.*, Feb. 2003; 14(2):209-14.

Zaugg et al., "Current concepts on ventricular fibrillation: a vicious circle of cardiomyocyte calcium overload in the initiation, maintenance, and termination of ventricular fibrillation," *Indian Pacing and Electrophysiology Journal*, Apr. 2004; 4(2):85-92.

Zhang et al., "Acute atrial arrhythmogenicity and altered Ca(2+) homeostasis in murine RyR2-P2328S hearts," *Cardiovascular Research*, Mar. 2011; 89(4):794-804.

Zoghi et al., "Electrical stunning and hibernation: suggestion of new terms for short- and long-term cardiac memory," *Europace*, Sep. 2004; 6(5):418-24.

Zografos et al., "Inhibition of the renin-angiotensin system for prevention of atrial fibrillation," *Pacing Clin Electrophysiol.*, Oct. 2010; 33(10):1270-85.

C00005397.WOU4 (PCT/US2014/066792) PCT Notification of Transmittal of the International Search Report and the Written Opinion of the International Searching Authority.

C00001726.WOU3 (PCT/US2014/013601) PCT Notification of Transmittal of the International Search Report and the Written Opinion of the International Searching Authority.

C00005682.WOU3 (PCT/US2014/036782) PCT Notification of Transmittal of the International Search Report and the Written Opinion of the International Searching Authority, dated Aug. 22, 2014, 11 pages.

International Search Report and Written Opinion for Application No. PCT/US2017/047378, 8 pages, dated Dec. 6, 2017.

C00015339.WO01 (PCT/US2018/050988) PCT Notification of Transmittal of the International Search Report and the Written Opinion of the International Searching Authority, dated Nov. 14, 2018, 11 pages.

C00015339.WO02 (PCT/US2018/050993) PCT Notification of Transmittal of the International Search Report and the Written Opinion of the International Searching Authority, dated Nov. 16, 2018, 7 pages.

C00019193WO01 ( PCT US2019/023642) PCT Notification of Transmittal of the International Search Report and the Written Opinion of the International Searching Authority, dated Jun. 28, 2019, 14 pages.

C00018366.WO01 (PCT/US2019/023645) PCT Notification of Transmittal of the International Search Report and the Written Opinion of the International Searching Authority, dated Sep. 4, 2019, 14 pages.

C00019138.WO01 (PCT/US2019/023646) PCT Notification of Transmittal of the International Search Report and the Written Opinion of the International Searching Authority, dated Aug. 19, 2019, 15 pages.

C00019428. WO01 (PCT/IB2019/057352) PCT Notification of Transmittal of the International Search Report and the Written Opinion of the International Searching Authority, dated Nov. 27, 2019, 123 pages.

International Search Report and Written Opinion for Application No. PCT/US2020/023525, 10 pages, dated Jul. 9, 2020.

\* cited by examiner

VFA DELIVERY AND IMPLANT REGION DETECTION

The present application claims the benefit of U.S. Provisional Application No. 62/891,599, filed Aug. 26, 2019, which is incorporated herein by reference in its entirety.

The present technology is generally related to implantable medical systems, in particular, to delivering implantable medical systems.

The cardiac conduction system includes the sinus atrial (SA) node, the atrioventricular (AV) node, the bundle of His, bundle branches, and Purkinje fibers. A heartbeat is initiated in the SA node, which may be described as the natural "pacemaker" of the heart. An electrical impulse arising from the SA node causes the atrial myocardium to contract. The signal is conducted to the ventricles via the AV node which inherently delays the conduction to allow the atria to stop contracting before the ventricles begin contracting thereby providing proper AV synchrony. The electrical impulse is conducted from the AV node to the ventricular myocardium via the bundle of His, bundle branches, and Purkinje fibers.

Implantable medical devices (IMDs), such as cardiac pacemakers or implantable cardioverter defibrillators, deliver therapeutic stimulation to patients' hearts. Patients with a conduction system abnormality, such as poor AV node conduction or poor SA node function, may receive an IMD, such as a pacemaker, to restore a more normal heart rhythm and AV synchrony. Some types of IMDs, such as cardiac pacemakers, implantable cardioverter-defibrillators (ICDs), or cardiac resynchronization therapy (CRT) devices, provide therapeutic electrical stimulation to a heart of a patient via electrodes on one or more implantable endocardial, epicardial, or coronary venous leads that are positioned in or adjacent to the heart. The therapeutic electrical stimulation may be delivered to the heart in the form of pulses or shocks for pacing, cardioversion, or defibrillation. In some cases, an IMD may sense intrinsic depolarizations of the heart and control the delivery of therapeutic stimulation to the heart based on the sensing.

Delivery of therapeutic electrical stimulation to the heart can be useful in addressing cardiac conditions such as ventricular dyssynchrony that may occur in patients. Ventricular dyssynchrony may be described as a lack of synchrony or a difference in the timing of contractions in different ventricles of the heart. Significant differences in timing of contractions can reduce cardiac efficiency. CRT, delivered by an IMD to the heart, may enhance cardiac output by resynchronizing the electromechanical activity of the ventricles of the heart. CRT is sometimes referred to as "triple chamber pacing" because CRT delivers pacing to three chambers, namely, the right atrium, right ventricle, and left ventricle.

Cardiac arrhythmias may be treated by delivering electrical shock therapy for cardioverting or defibrillating the heart in addition to cardiac pacing, for example, from an ICD, which may sense a patient's heart rhythm and classify the rhythm according to an arrhythmia detection scheme in order to detect episodes of tachycardia or fibrillation. Arrhythmias detected may include ventricular tachycardia (VT), fast ventricular tachycardia (FVT), ventricular fibrillation (VF), atrial tachycardia (AT) and atrial fibrillation (AT). Anti-tachycardia pacing (ATP), a painless therapy, can be used to treat ventricular tachycardia (VT) to substantially terminate many monomorphic fast rhythms. While ATP is painless, ATP may not deliver effective therapy for all types of VTs. For example, ATP may not be as effective for polymorphic VTs, which has variable morphologies. Polymorphic VTs and ventricular fibrillation (VFs) can be more lethal and may require expeditious treatment by shock.

Dual chamber medical devices are available that include a transvenous atrial lead carrying electrodes that may be placed in the right atrium and a transvenous ventricular lead carrying electrodes that may be placed in the right ventricle via the right atrium. The dual chamber medical device itself is generally implanted in a subcutaneous pocket and the transvenous leads are tunneled to the subcutaneous pocket. A dual chamber medical device may sense atrial electrical signals and ventricular electrical signals and can provide both atrial pacing and ventricular pacing as needed to promote a normal heart rhythm and AV synchrony. Some dual chamber medical devices can treat both atrial and ventricular arrhythmias.

Intracardiac medical devices, such as a leadless pacemaker, have been introduced or proposed for implantation entirely within a patient's heart, eliminating the need for transvenous leads. A leadless pacemaker may include one or more electrodes on its outer housing to deliver therapeutic electrical signals and/or sense intrinsic depolarizations of the heart. Intracardiac medical devices may provide cardiac therapy functionality, such as sensing and pacing, within a single chamber of the patient's heart. Single chamber intracardiac devices may also treat either atrial or ventricular arrhythmias or fibrillation. Some leadless pacemakers are not intracardiac and may be positioned outside of the heart and, in some examples, may be anchored to a wall of the heart via a fixation mechanism.

SUMMARY

The techniques of this disclosure generally relate to delivering an implantable medical system for ventricle-from-atrium (VfA) cardiac therapy. These techniques may facilitate accurate delivery of an implantable medical system through the triangle of Koch region in the right atrium for pacing the left ventricle. In particular, at least one electrode of an implantable lead or device may be advanced from the triangle of Koch region through the right atrial endocardium and central fibrous body into the left ventricular myocardium of the patient's heart to deliver cardiac therapy to or sense electrical activity of the left ventricle in the basal region, septal region, or basal-septal region of the left ventricular myocardium. An atrial slow pathway potential (ASP) may be used to determine the suitability of a pacing location or depth for VfA cardiac therapy.

In one aspect, a method includes locating the triangle of Koch region in the right atrium of a patient's heart; securing at least one electrode of an implantable lead or device to cardiac tissue from the triangle of Koch region to deliver ventricle-from-atrium (VfA) cardiac therapy; and testing the location or depth of the at least one electrode to configure VfA cardiac therapy. An atrial slow pathway potential (ASP) may be used to determine the suitability of a pacing location or depth for VfA cardiac therapy. A delivery system including a mapping analyzer may be used to carry out the method.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
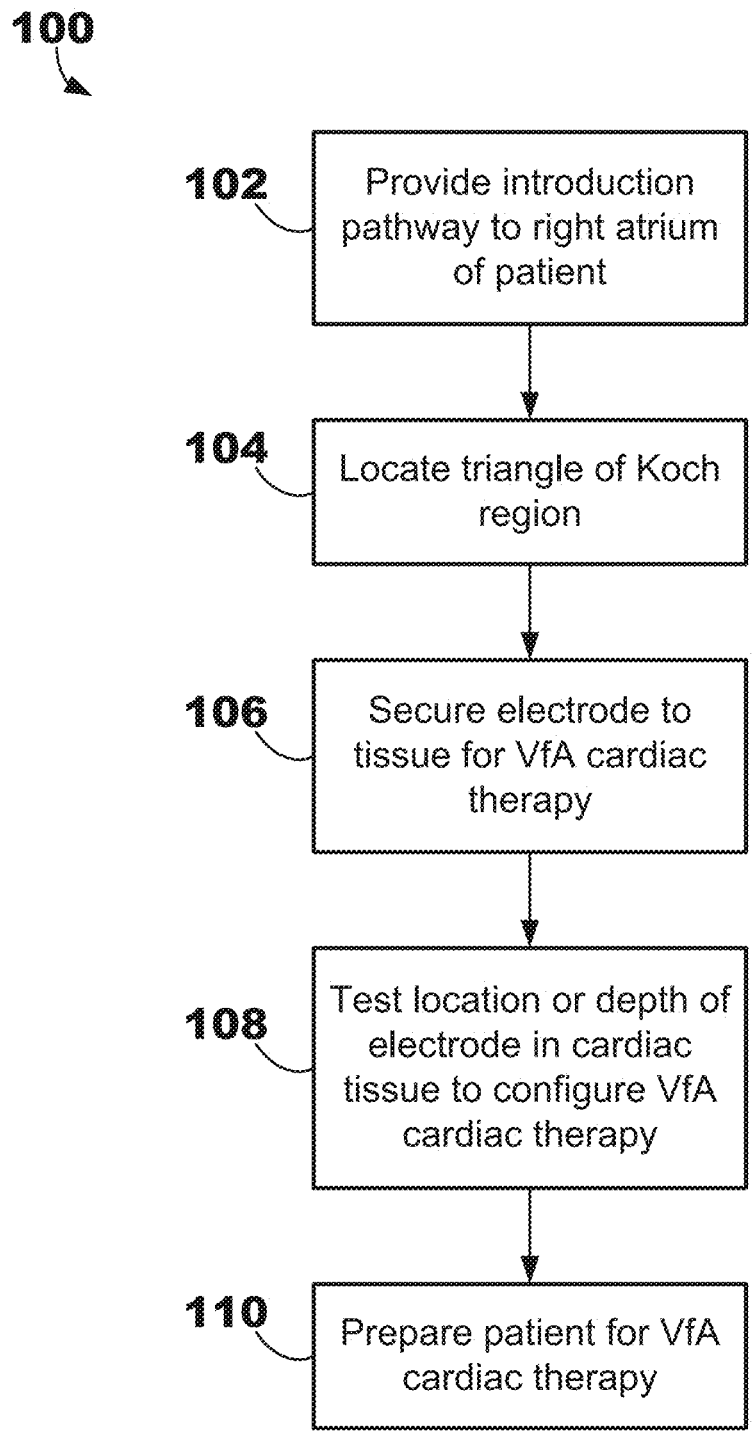
FIG. 1 is a flow diagram that illustrates one example of a method for delivering an implantable medical system including a lead or device for VfA cardiac therapy.

The present disclosure provides techniques for delivering an implantable medical system for VfA cardiac therapy. These techniques may facilitate accurate delivery of an implantable medical system through the triangle of Koch region in the right atrium (RA) for pacing the left ventricle (LV). In particular, at least one electrode of an implantable lead or device may be advanced from the triangle of Koch region through the RA endocardium and central fibrous body into the LV myocardium of the patient's heart to deliver cardiac therapy to or sense electrical activity of the LV in the basal region, septal region, or basal-septal region of the LV myocardium.

As used herein, the term "or" is generally employed in its inclusive sense, for example, to mean "and/or" unless the context clearly dictates otherwise. The term "and/or" means one or all the listed elements or a combination of at least two of the listed elements.

The terms "coupled" or "connected" refer to elements being attached to each other either directly (i.e., in direct contact with each other) or indirectly (i.e., having one or more elements between and attaching the two elements). Either term may be modified by "operatively" and "operably," which may be used interchangeably, to describe that the coupling or connection is configured to allow the components to interact to carry out functionality described in this disclosure or known to one skilled in the art having the benefit of this disclosure.

Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIGS. 1-5 show various methods that may be used to deliver an implantable lead or device for VfA cardiac therapy. FIG. 1 shows an overall method, whereas FIGS. 2-5 show detail of some parts of the overall method. Some or all steps of these methods may be carried out by a physician, or other qualified medical professional, who may be assisted by various systems and devices described herein, for example, with respect to FIGS. 7-9. Some examples of implantation locations targeted by these various methods are shown in FIG. 6.

FIG. 1 is a flow diagram that illustrates one example of a method 100 for delivering an implantable medical system including a lead or device for VfA cardiac therapy. In general, VfA cardiac therapy may include single or multiple chamber pacing (e.g., dual or triple chamber pacing), atrioventricular (AV) synchronous pacing, asynchronous pacing, triggered pacing, cardiac resynchronization pacing, or tachycardia-related therapy. In some embodiments, VfA cardiac therapy utilizes at least one electrode coupled to the implantable lead or device implanted in the basal region, septal region, or basal-septal region (basal and septal region) of the LV myocardium of the patient's heart from the triangle of Koch region of the RA through the RA endocardium and central fibrous body. The electrode may be described as a tissue piercing electrode. The basal, septal, basal-septal regions are described in more detail with respect to FIG. 6. The triangle of Koch region is described in more detail with respect to FIGS. 7-8.

The method 100 may include providing an introduction pathway to the RA of the patient's heart 102 from outside of the patient's body to deliver at least one electrode to the RA of the patient's heart. In general, the introduction pathway to the RA includes a vein near a surface of the patient's body that leads to the RA.

The method 100 may also include locating the triangle of Koch region in the right atrium of a patient's heart 104. In some cases, the triangle of Koch region may be found in relation to particular anatomical structures, such as the tricuspid valve and the coronary sinus ostium (CSO) and the AV node, which may also be described as reference anatomical structures. In other words, the tricuspid valve or the CSO may be used as a starting point to find the triangle of Koch region.

Further, the method 100 may include securing at least one electrode of an implantable lead or device of the implantable medical system to cardiac tissue through the triangle of Koch region to deliver ventricle-from-atrium (VfA) cardiac therapy 106. Securing at least one electrode may include selecting a particular location, depth, or orientation of the implantable lead or device to properly position the at least one electrode. In general, securing at least one electrode of the implantable lead or device to cardiac tissue through the triangle of Koch region does not position the one or more electrodes into the blood volume of the LV of the patient's heart.

Also, the method 100 may include testing the location or depth of the at least one electrode to configure VfA cardiac therapy 108. If the initial location or depth of the at least one electrode is not sufficient for the desired VFA cardiac therapy, the electrode may be repositioned in terms of location or depth, for example, by adjusting the location, depth, or orientation of the implantable lead or device. Any suitable technique may be used to test the location or depth of the at least one electrode to configure VfA cardiac therapy 108, such as described with respect to FIG. 13 describing one example of identifying a location or depth for VfA cardiac therapy using an atrial slow pathway potential (ASP).

The method 100 may further include preparing a patient for VfA cardiac therapy 110. In general, any introducers or components unnecessary for delivering VfA cardiac therapy may be removed from the patient's body after the implantable medical system has been delivered. For example, a catheter may be slit, the introducer may be removed, the lead may be tied down (if there is a lead) and connected to a device (such as a pacemaker) placed in a pocket, and the pocket may be closed.

Figure 2:
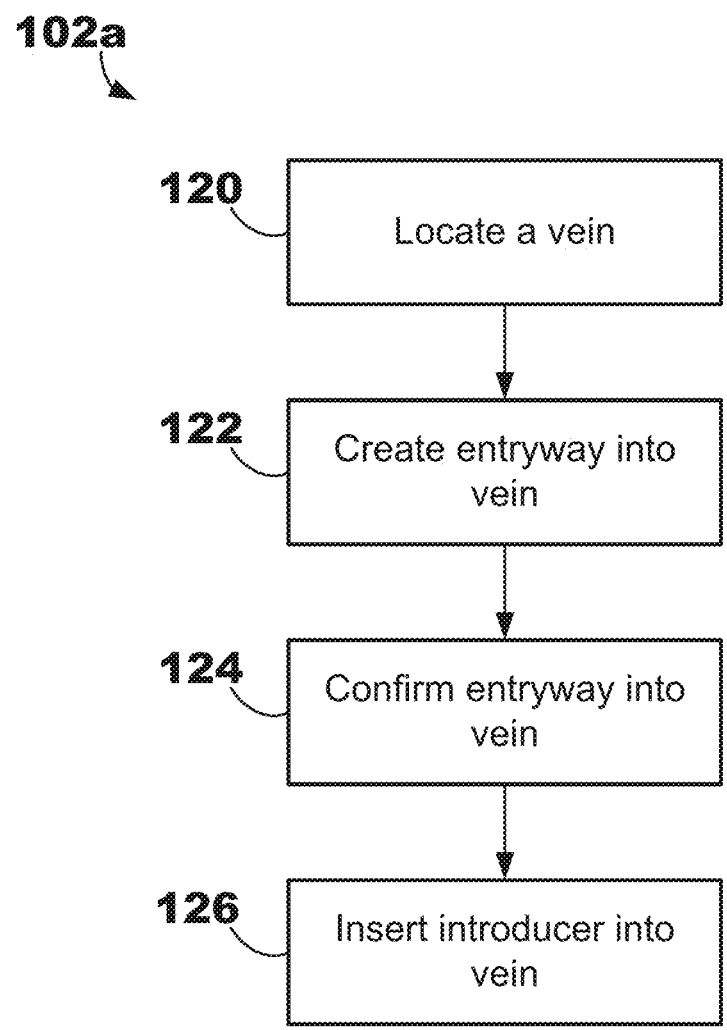
FIG. 2 is a flow diagram that illustrates one example of a method for providing an introduction pathway to the right atrium of the patient's heart that may be used with, for example, the method of FIG. 1.

FIG. 2 is a flow diagram that illustrates one example method 102a of providing an introduction pathway to the RA of the patient's heart 102. The method 102 may include locating a vein 120 that leads to the RA of the patient's heart. A physician may palpate the patient's body to find a vein leading to the patient's RA. In some embodiments, the subclavian vein may be used. However, any suitable vein leading to the patient's right atrium may be used. For example, the right atrium may be accessed via transvenous catheters placed through a femoral vein in the groin, as well as through superior veins such as the subclavian, brachiocephalic, or jugular veins.

The method 102a may also include creating an entryway into the vein 122. In some embodiments, a physician may insert a needle and syringe into the vein.

The method 102a may further include confirming that the entryway goes into the vein 124. For example, a physician may check that the needle has entered into the subclavian vein. In some embodiments, a physician may retract, or pull back on, the syringe to extract fluid from the entryway. If the color of the blood extracted into the syringe is purple, the physician may determine that the needle has entered into the subclavian vein or other suitable vein.

In addition, the method 102a may include inserting an introducer into the vein 126 through the entryway. In general, the introducer may be used to introduce various components of an implantable medical system or delivery system through the entryway and into the RA. One example of an introducer is a sheath that may be placed in the entryway through the syringe and needle, through the subclavian vein, and into the RA. The sheath may extend from outside of the patient's body into the RA. The implantable lead or device may be advanced from outside of the patient's body, through the sheath, and into the RA.

Figure 3:
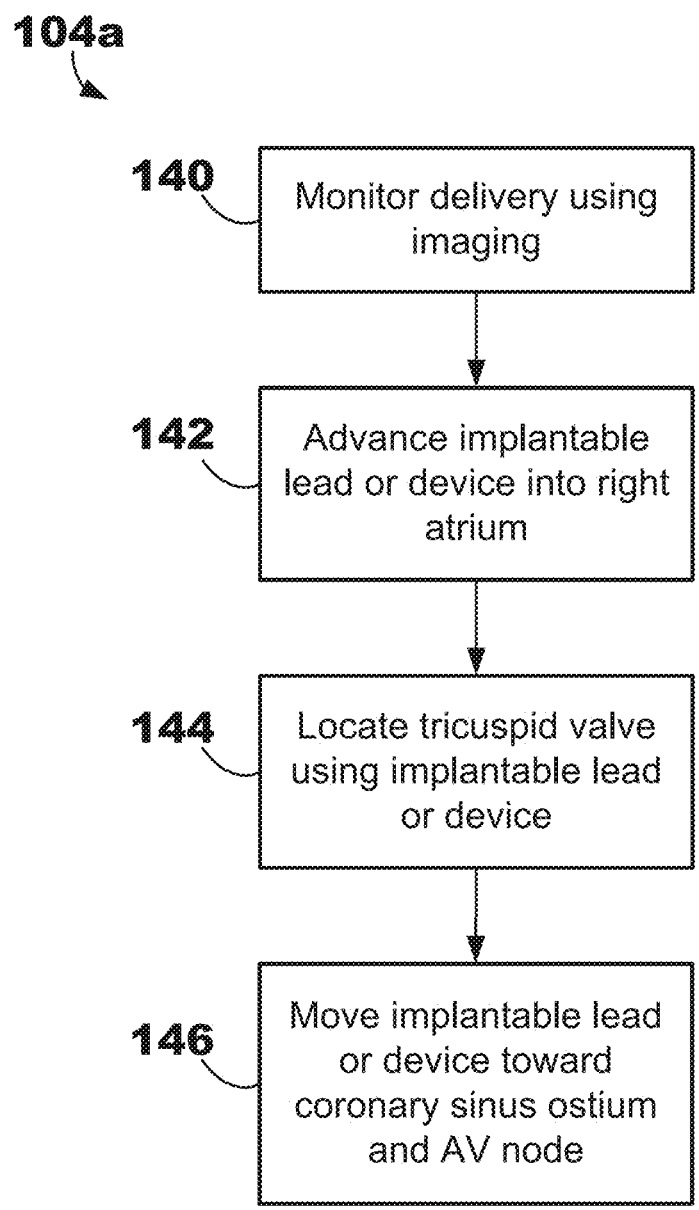
FIG. 3 is a flow diagram that illustrates a first example of a method for locating the triangle of Koch region in the patient's heart that may be used with, for example, the method of FIG. 1.

FIG. 3 is a flow diagram that illustrates a first example method 104a of locating the triangle of Koch region in the patient's heart 104. The method 104a may include monitoring delivery of at least one electrode using imaging 140. For example, an imaging device or system, such as an x-ray imaging system or echocardiogram system, may be used to view one or more components being advanced into the RA. In some embodiments, a component of the delivery system or a component of the implantable lead or device may include an imaging agent, such as a radiopaque material, to provide contrast and visibility when viewed using the x-ray imaging system. In addition, other imaging agents may be used, such as a fluoroscopic contrast dye.

The method 104a may also include advancing the implantable lead or device into the RA 142. When an introducer is used, such as a sheath, the implantable lead or device may be advanced through the introducer into the RA. The implantable lead, or delivery system for the device, may be steerable. A stylet may be coupled to the lead, or delivery system for the device, to provide a physician with control to steer the lead through the patient's body toward an implantation site.

The method 104a may further include locating the tricuspid valve of the patient's heart using the implantable lead or device 144. In some embodiments, a physician may locate the tricuspid valve, for example, by allowing the implantable lead or device to fall into the RV or slide the device along the RA endocardium until the implantable lead or device falls into the RV to locate the tricuspid valve. A ridge of the tricuspid valve proximate to the septal wall of the right atrium above the septal leaflet of the tricuspid valve may be located. In some embodiments, a physician may locate the ridge of the tricuspid valve by moving a distal end of the implantable lead or device along the tricuspid valve until a tactile response of the ridge is detected by the physician.

In addition, the method 104a may include moving the implantable lead or device partially toward the CSO and the AV node of the patient's heart to reach the triangle of Koch region 146, for example, after locating the tricuspid valve. In some embodiments a distal end of the implantable lead or device may be moved along the endocardium of the RA a certain distance before reaching triangle of Koch region. For example, the distal end of the implantable lead or device may be moved between 3 and 5 mm in a direction toward the CSO and the AV node. This distance is shorter than the distance required to reach either the CSO or AV node.

Figure 4:
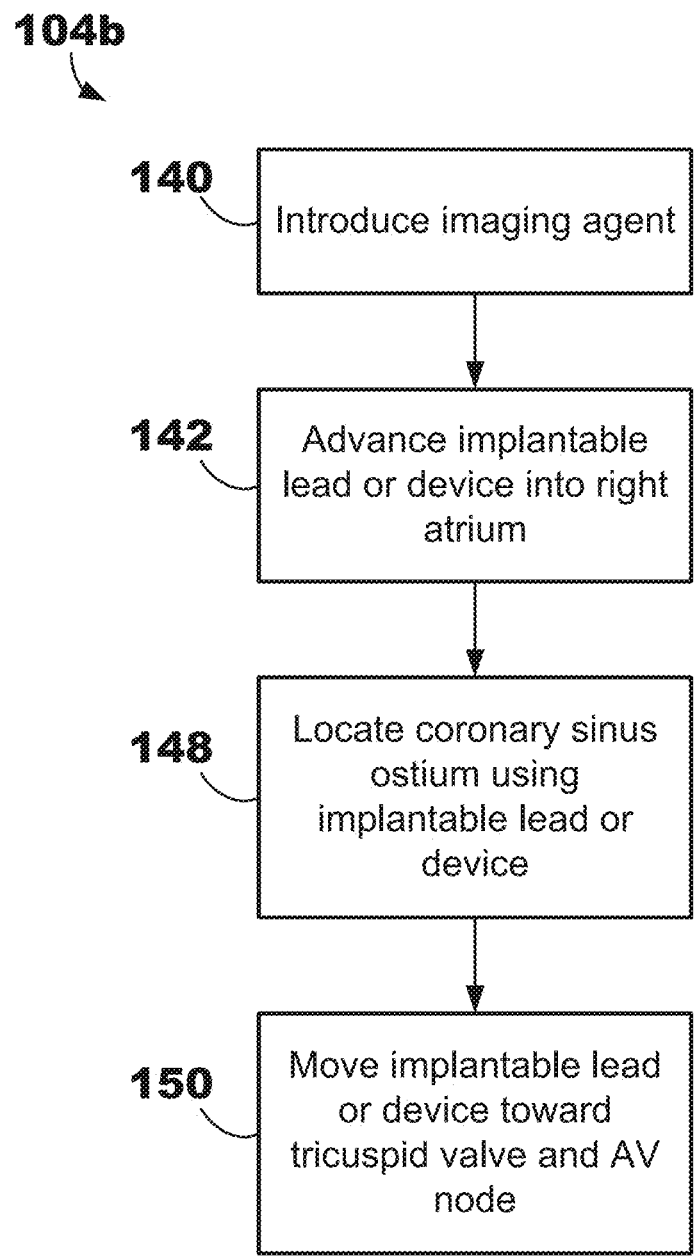
FIG. 4 is a flow diagram that illustrates a second example of a method for locating the triangle of Koch region in the patient's heart that may be used with, for example, the method of FIG. 1.

FIG. 4 is a flow diagram that illustrates a second example method 104b of locating the triangle of Koch region in the patient's heart 104. The method 104b is similar to the method 104a and that the method 104b may include monitoring delivery of at least one electrode using imaging 140 and advancing the implantable lead or device into the RA 142. In general, both methods 104a, 104b use the implantable lead or device to locate an anatomical structure that helps to locate the triangle of Koch region.

Differing from the method 104a, the method 104b may include locating the CSO using the implantable lead or device 148. In some embodiments, locating the CSO may include advancing the implantable lead or device into the coronary sinus (CS) of the patient's heart, which may be described as cannulating the CS. The implantable lead or device may be retracted from the CS until a distal end of the implantable lead or device reaches the CSO, just outside of the CS, based on fluoroscopy landmarks. Imaging agents may be used to highlight the CSO and the tricuspid valve.

The method 104b may also include moving the implantable lead or device partially toward the tricuspid valve and the AV node to reach the triangle of Koch region 150. In some embodiments a distal end of the implantable lead or device may be moved along the endocardium of the RA a certain distance before reaching triangle of Koch region. For example, the distal end of the implantable lead or device may be moved between 3 and 5 mm in a direction toward the tricuspid valve and the AV node. This distance is shorter than the distance required to reach either the tricuspid valve or AV node.

Figure 5:
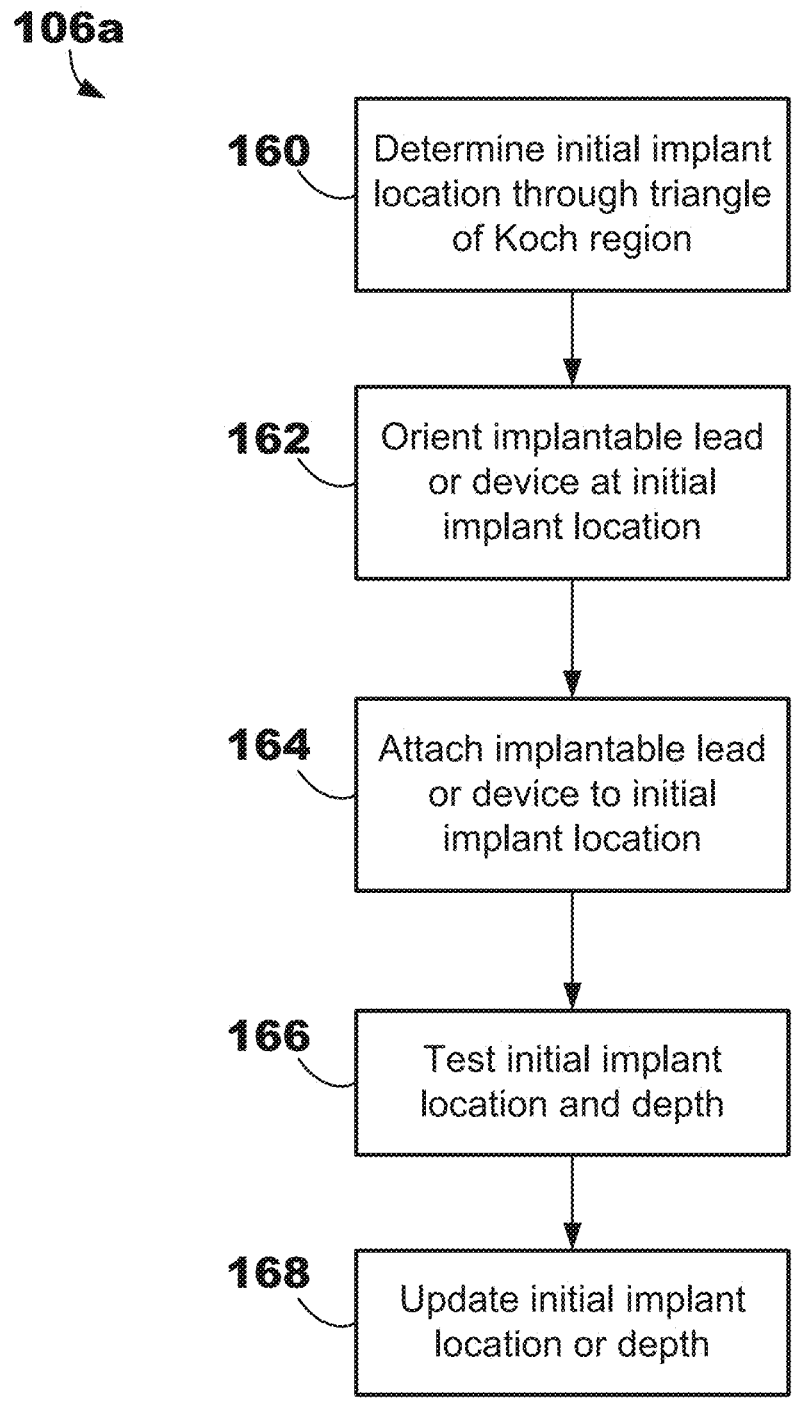
FIG. 5 is a flow diagram that illustrates one example of a method for testing the location or depth of at least one electrode coupled to cardiac tissue from the triangle of Koch region that may be used with, for example, the method of FIG. 1.
Figure 6:
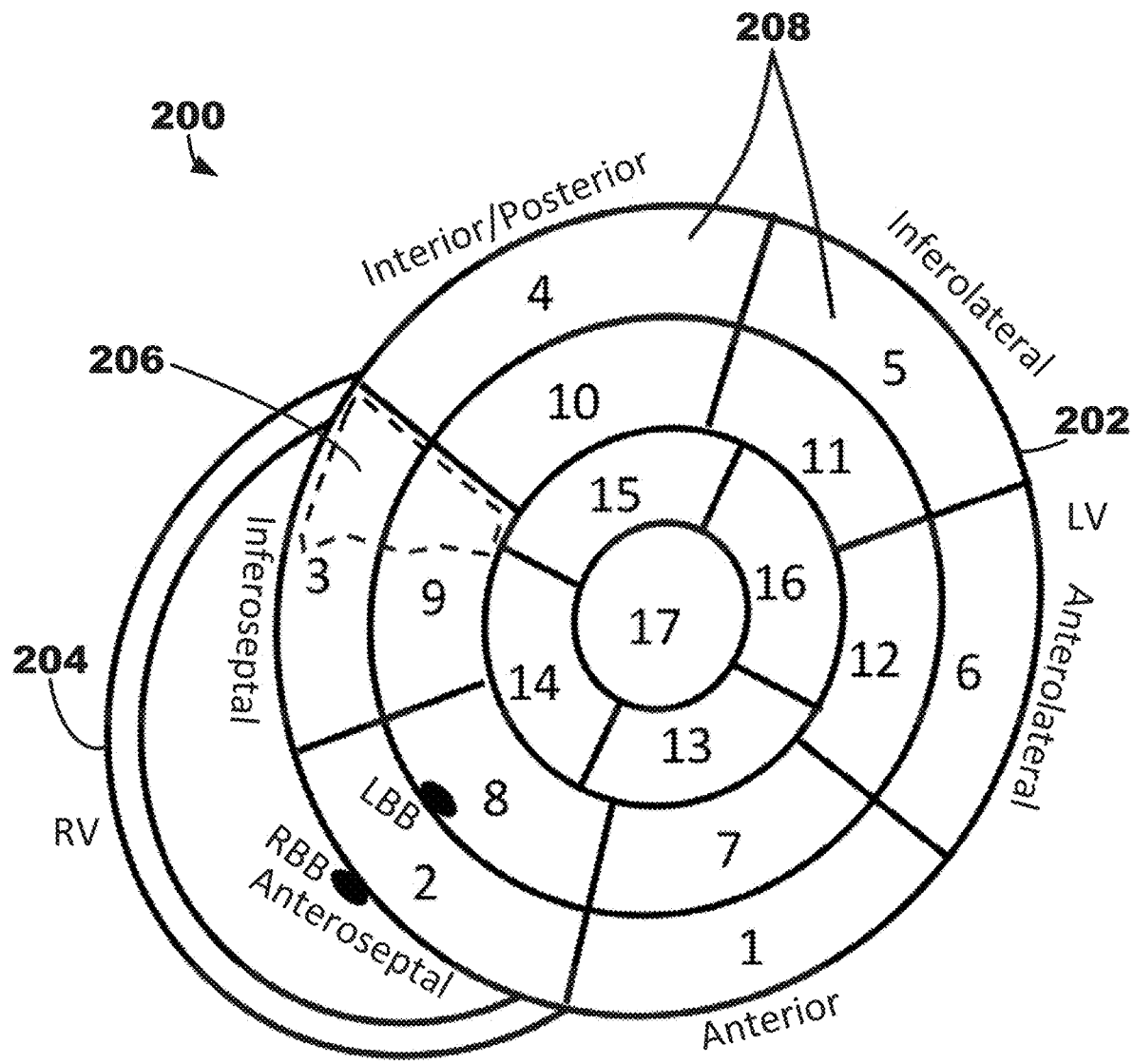
FIG. 6 is a conceptual diagram that shows electrode implantation locations relative to a map of a patient's heart in a standard 17 segment view for reference during use with, for example, the methods of FIGS. 1-5.

FIG. 5 is a flow diagram that illustrates one example method 106a for testing the location or depth of at least one electrode coupled to cardiac tissue from the triangle of Koch region 106. Testing the location or depth of the at least one electrode may help to ensure that the electrode will be suitable for use in delivering VfA cardiac therapy.

The method 106a may include determining an initial implant location through the triangle of Koch region 160. For example, the initial implant location may be based on moving a distal end of the implantable lead or device a particular distance from the tricuspid valve or CSO.

The method 106a may also include orienting the implantable lead or device at the initial implant location 162. In some embodiments, orienting the implantable lead or device may include pointing a distal end of the implantable lead or device toward the LV apex of the patient's heart. Orienting the implantable lead or device may be defined using a longitudinal axis that extends along the elongate lead or device. In some embodiments orienting the implantable lead or device may include aligning a longitudinal axis of the implantable lead or device, or a longitudinal axis of a distal end portion of the implantable lead or device, orthogonal (or perpendicular) to the surface of the triangle of Koch region at the initial implant location.

The method 106a may also include attaching the implantable lead or device to the initial implant location 164. The implantable lead or device may be attached in any suitable manner, which may depend on the type of fixation mechanism is included. In some embodiments, the implantable lead or device includes a helical fixation assembly, which may be part of a tissue penetrating assembly including one or more electrodes. The implantable lead or device may be attached by rotating, or screwing clockwise or counterclockwise, the implantable lead or device to advance the at least one electrode into cardiac tissue forming the triangle of Koch region toward the LV. In some embodiments, the implantable lead or device includes fixation elements, which may be separate from the tissue penetrating assembly including one or more electrodes. Fixation elements may be in the form of tines that engage with cardiac tissue forming the triangle of Koch region.

The method 106a may further include testing the initial implant location or depth 166. Any suitable testing may be performed to verify the ability of the at least one electrode to deliver VfA cardiac therapy. In some embodiments, testing may include monitoring electrical activity using one or more electrodes of the implantable lead or device. Testing may also include monitoring mechanical activity using a motion sensor of the implantable lead or device. Further, testing may include delivering test pulses using one or more electrodes of the implantable lead or device detectable by an external electrode apparatus, such as the apparatus described with respect to FIG. 9. Various pacing configurations or parameters may be tested at each location and depth.

In addition, the method 106a may include updating the initial implant location or depth in response to the testing 168. If the testing indicates that the at least one electrode is not properly positioned to deliver VfA cardiac therapy, the initial implant location or depth may be changed. In one example, the implantable lead or device may be retracted from the cardiac tissue and reoriented at the same implant location. In another example, the implantable lead or device may be retracted from the cardiac tissue and relocated to another implantation site through the triangle of Koch region. In a further example, the implantable lead or device may be inserted further into the cardiac tissue at the same implant location. The depth may be adjusted by rotating the implantable lead or device, for example, when a helical fixation assembly is used.

Various steps of the method 106a may be repeated until the testing indicates that the at least one electrode is properly positioned to deliver VfA cardiac therapy. Updating the initial implant location or depth 168 may only be performed, in some cases, if the at least one electrode is not properly positioned to deliver VFA cardiac therapy.

FIG. 6 is a two-dimensional (2D) ventricular map 200 of a patient's heart (e.g., a top-down view) showing the LV 202 in a standard 17 segment view and the right ventricle (RV) 204. The map 200 includes a plurality of areas 208 corresponding to different regions of a human heart. As illustrated, the areas 208 are numerically labeled 1-17 (which, e.g., correspond to a standard 17 segment model of a human heart, correspond to 17 segments of the left ventricle of a human heart, etc.). Areas 208 of the map 200 may include basal anterior area 1, basal anteroseptal area 2, basal inferoseptal area 3, basal inferior area 4, basal inferolateral area 5, basal anterolateral area 6, mid-anterior area 7, mid-anteroseptal area 8, mid-inferoseptal area 9, mid-inferior area 10, mid-inferolateral area 11, mid-anterolateral area 12, apical anterior area 13, apical septal area 14, apical inferior area 15, apical lateral area 16, and apex area 17. The inferoseptal and anteroseptal areas of the right ventricle 204 are also illustrated, as well as the right bunch branch (RBB) and left bundle branch (LBB).

In some embodiments, a tissue piercing electrode may be implanted in a target implant region in the basal region, septal region, or basal-septal region of the LV myocardium of the patient's heart, for example, through or from the triangle of Koch region of the RA through the RA endocardium and central fibrous body. With reference to map 200, the basal region includes one or more of the basal anterior area 1, basal anteroseptal area 2, basal inferoseptal area 3, basal inferior area 4, mid-anterior area 7, mid-anteroseptal area 8, mid-inferoseptal area 9, and mid-inferior area 10. With reference to map 200, the septal region includes one or more of the basal anteroseptal area 2, basal anteroseptal area 3, mid-anteroseptal area 8, mid-inferoseptal area 9, and apical septal area 14. The basal-septal region may include one or more of the basal anteroseptal area 2, basal inferoseptal area 3, mid-anteroseptal area 8, and mid-inferoseptal area 9.

In some embodiments, the target implant region may include the basal inferoseptal area 3, mid-inferoseptal area 9, at least part of basal anteroseptal area 2 near the basal inferoseptal area, and at least part of mid-anteroseptal area 8 near the mid-inferoseptal area.

In some embodiments, the tissue piercing electrode may be positioned in the high inferior/posterior basal-septal region of the LV myocardium when implanted. The high inferior/posterior basal-septal region of the LV myocardium may include a portion of at least one of the basal inferoseptal area 3 and mid-inferoseptal area 9. For example, the high inferior/posterior basal septal region may include region 206 illustrated generally as a dashed-line boundary. As shown, the dashed line boundary represents an approximation of about where the high inferior/posterior basal-septal region and may take somewhat different shape or size depending on the particular application. Without being bound by any particular theory, intraventricular synchronous pacing or activation may result from stimulating the high septal ventricular myocardium due to functional electrical coupling between the subendocardial Purkinje fibers and the ventricular myocardium.

Figure 7:
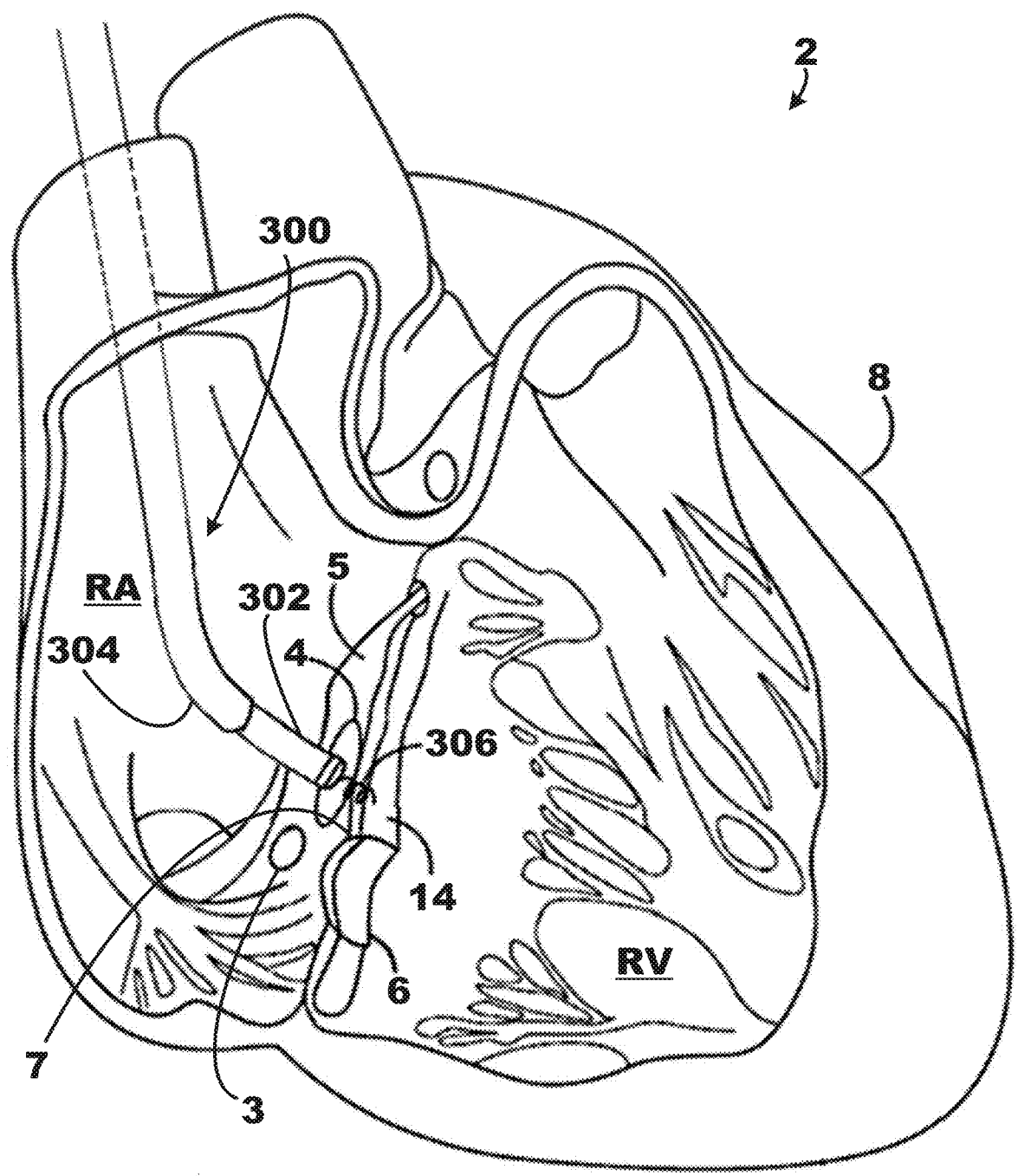
FIG. 7 is a perspective diagram that illustrates an implantable medical system including an implantable lead and delivery sheath for use with, for example, the methods of FIGS. 1-5.

FIG. 7 is one example of an implantable medical system, or cardiac therapy system, 300 in use with a patient 2 to deliver VfA cardiac therapy, which may be delivered using the methods of FIGS. 1-5. The system 300 may include one or more implantable medical leads or devices (which may be referred to as IMDs). In the illustrated embodiment, the system 300 includes including an implantable lead 302, which may also be described as a leaded medical device or implantable medical lead, that may be configured for single or multiple chamber therapy and implanted in a patient's heart 8. The implantable lead 302 may be advanced into the RA through an introducer 304, which may include a sheath extending through the subclavian vein into the RA.

The implantable lead 302 is shown implanted in RA of the patient's heart 8 in a target implant region 4, through which a tissue piercing electrode 306 may be advanced through the target implant region into a target implant location in the LV myocardium. In the illustration, the LV is behind the RV (see different perspective of the RV 614 and LV 618 of FIG. 10). In particular, the implantable lead 302 may include a tissue piercing electrode 306 that may be implanted in the high basal and/or septal region of the left ventricular myocardium 14 of the patient's heart from the triangle of Koch region of the right atrium through the right atrial endocardium and central fibrous body. In some embodiments, the tissue piercing electrode 306 may include or form part of a helical fixation assembly. The implantable lead 302 may be described as a ventricle-from-atrium (VfA) lead or device, which may sense or provide therapy to one or both ventricles (e.g., right ventricle, left ventricle, or both ventricles, depending on the circumstances) while being generally disposed in the RA.

The implantable lead 302 may include one or more fixation members (such as fixation members 20 in FIG. 8) that anchor a distal end of the implantable lead 302 against the atrial endocardium in a target implant region 4. The target implant region 4 may lie between the Bundle of His 5 and the coronary sinus ostium 3 and may be adjacent to a left side ridge 7 the tricuspid valve 6.

The one or more IMDs of the system 300 may include leadless or leaded IMDs. As used herein, a "leadless" device refers to a device being free of a lead extending out of the patient's heart 8. In other words, a leadless device may have a lead that does not extend from outside of the patient's heart 8 to into the inside of the patient's heart. Some leadless devices may be introduced through a vein, but once implanted, the device is free of, or may not include, any transvenous lead and may be configured to provide cardiac therapy without using any transvenous lead. In one example, a leadless device implanted in the RA, in particular, does not use a lead to operably connect to an electrode in the RA or LV when a housing of the device is positioned in the RA.

Figure 8:
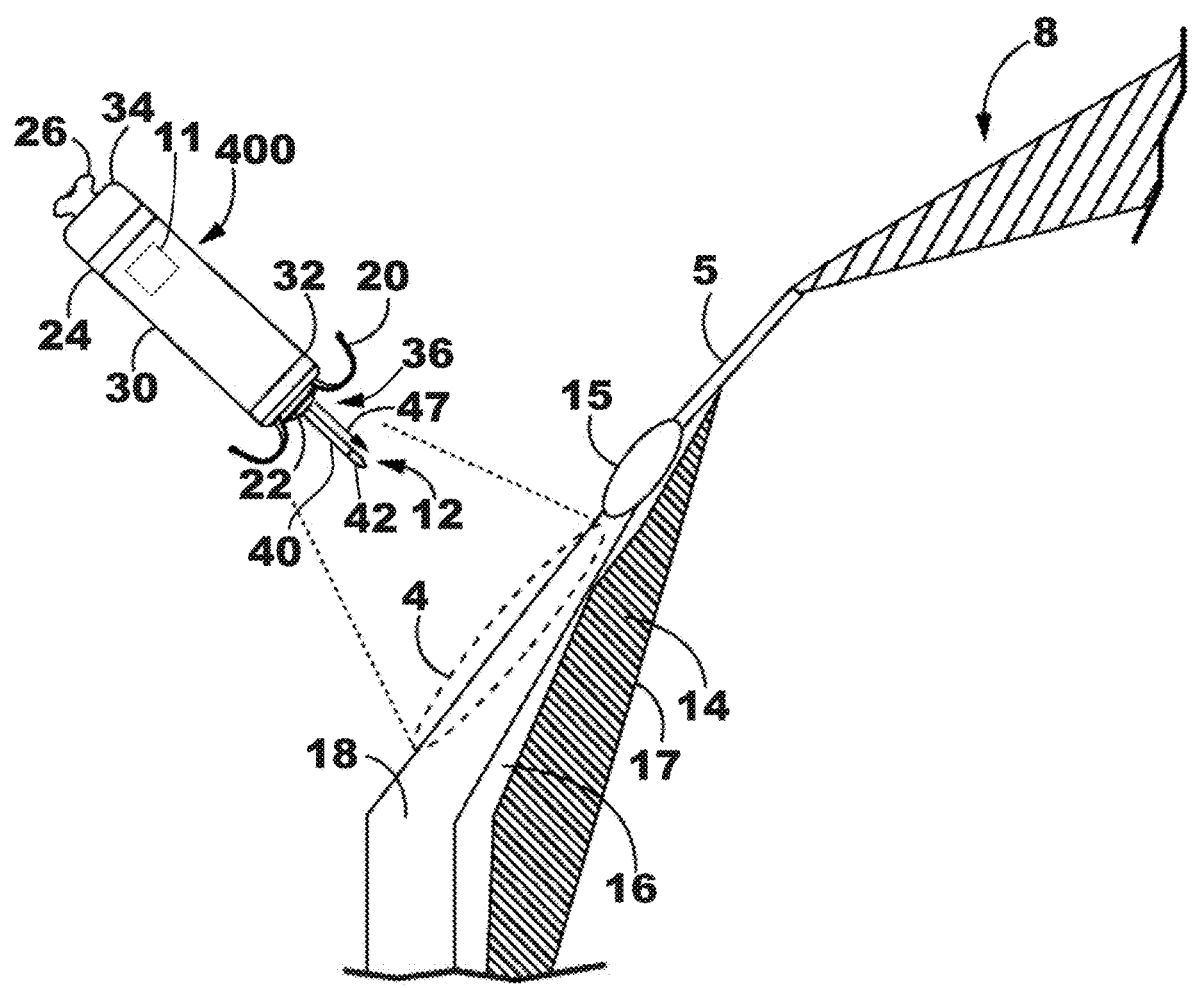
FIG. 8 is a perspective diagram that illustrates an implantable device for use with, for example, the methods of FIGS. 1-5.

The system 300 may include one or more intracardiac IMDs, such as implantable device 400 (FIG. 8). As used herein, an "intracardiac" device refers to a device configured to be implanted entirely within the heart 8. An intracardiac IMD may include an optional leadlet, which does not extend out of the patient's heart 8.

In some embodiments, the system 300 may include multiple electrodes. A first electrode of the system 300 may be configured to sense electrical activity of the LV of the patient's heart 8 or to deliver cardiac therapy to the LV of the patient's heart. A second electrode of the system 300 may be configured to sense electrical activity of the RA of the patient's heart 8 or to deliver cardiac therapy to the RA of the patient's heart.

One or more leadless electrodes may be coupled to the housing of an IMD. An IMD having only leadless electrodes may be described as a leadless IMD. As used herein, a "leadless" electrode refers to an electrode operably coupled to a device being free of a lead, or without using a lead, extending between the electrode and the housing of the device.

A motion sensor of the system 300 may be configured to sense mechanical activity of the patient's heart 8. In some cases, the motion sensor may be configured to sense at least mechanical activity of an atrium of the patient's heart 8. The motion sensor used may be the same as or similar to the motion sensor 11 (FIG. 8). A controller of the system 300, which may include processing circuitry, may be operably coupled to one or more of the electrodes and to the motion sensor. The operable coupling may be made using a wired or wireless connection.

In the illustrated embodiment, the system 300 includes an implantable lead 302. The implantable lead 302 may be configured to sense electrical activity of the heart 8 and to deliver pacing therapy, such as CRT. The implantable lead 302 may be attached to an interior wall (such as AV septal wall 662 shown in FIG. 12) of the heart 8 via one or more fixation elements that penetrate the tissue. These fixation elements may secure the implantable lead 302 to the cardiac tissue and retain an electrode (e.g., a cathode or an anode) on the housing of the first medical device in contact with the cardiac tissue, such as the endocardium or the myocardium. In addition to delivering pacing pulses, the implantable lead 302 may be configured to sense or monitor electrical activity, in the form of one or more electrical signals, using the electrodes carried on the housing of the implantable lead 302. The electrical activity may be generated by cardiac muscle and indicative of depolarizations and repolarizations of the heart 8 at various times during the cardiac cycle.

Processing circuitry, sensing circuitry, and other circuitry configured for performing the techniques described herein with respect to the implantable lead 302 may be housed within a respective sealed housing (not shown) operably coupled to the implantable lead. The housing (or a portion thereof) may be conductive to serve as an electrode for pacing or sensing, or as an active electrode during defibrillation. As such, the housing of an IMD may be described as including a housing electrode, or housing-based electrode.

FIG. 8 shows one example of an intracardiac or leadless implantable medical device 400 and anatomical structures of the patient's heart 8 that may be used with a cardiac therapy system, which may be leadless. The device 400 may be used as an alternative to the lead 302 (FIG. 7). In other words, the device 400 and the lead 302 may be interchangeable in terms of functionality to deliver VfA cardiac therapy once implanted.

The intracardiac device 400 may include a housing 30. The housing 30 may define a hermetically-sealed internal cavity in which internal components of the device 400 reside, such as a sensing circuit, therapy delivery circuit, control circuit, memory, telemetry circuit (or communication interface), other optional sensors, and a power source. The housing 30 may be at least partially formed from electrically conductive material. Additionally, or alternatively, the housing 30 may be formed at least partially from non-conductive material.

The housing 30 may be described as extending between a distal end region 32 and a proximal end region 34 in a generally cylindrical shape to facilitate delivery. The housing 30 may include a delivery tool interface member 26, e.g., at the proximal end 34, for engaging with a delivery tool during implantation of the device 400. For example, the delivery tool interface member 26 may be used while the device 400 is advanced toward a target implant region 4 using a delivery catheter. The delivery tool or catheter may be steerable to direct the device 400 toward the target implant region 4.

All or a portion of the housing 30 may function as an electrode during cardiac therapy, for example, in sensing and/or pacing. In the example shown, the housing-based electrode 24 is shown to circumscribe a proximal portion of the housing 30. When the housing 30 includes (e.g., is formed from) an electrically conductive material, portions of the housing 30 may be electrically insulated by a non-conductive material, such as a coating, leaving one or more discrete areas of conductive material exposed to define the proximal housing-based electrode 24. When the housing 30 includes (e.g., is formed from) a non-conductive material, an electrically conductive coating or layer may be applied to one or more discrete areas of the housing 30 to form the proximal housing-based electrode 24. In other examples, the proximal housing-based electrode 24 may be a component, such as a ring electrode, that is mounted or assembled onto the housing 30. The proximal housing-based electrode 24 may be electrically coupled to internal circuitry of the device 400, e.g., via the electrically-conductive housing 30 or an electrical conductor when the housing 30 includes a non-conductive material.

In the example shown, the housing-based electrode 24 is located nearer to the housing proximal end region 34 than the housing distal end region 32 and may, therefore, be described as being a proximal housing-based electrode. In other examples, however, the housing-based electrode 24 may be located at other positions along the housing 30, for example, relatively more distally than the position shown.

At the distal end region 32, the device 400 may include a distal fixation and electrode assembly 36, which may include one or more fixation members 20, in addition to one or more dart electrodes 12 of equal or unequal length. The one or more dart electrodes 12 of the assembly 36 may be described as tissue piercing electrodes. In other embodiments (not shown), the distal fixation and electrode assembly 36 may include a helical or spiral-shaped electrode. A dart electrode or a helix electrode may also be described as a tissue piercing electrode.

The device 400 as depicted includes a single dart electrode 12 that may include a shaft 40 extending distally away from the housing distal end region 32 and may include one or more electrode elements, such as a tip electrode element 42 at or near the free, distal end region of the shaft 40. The tip electrode element 42 may have a conical or hemispherical distal tip with a relatively narrow tip diameter (e.g., less than about 1 millimeter (mm)) for penetrating into and through tissue layers without using a sharpened tip or needle-like tip having sharpened or beveled edges.

The shaft 40 of the dart electrode 12 may be a normally straight member and may be rigid. In other embodiments, the shaft 40 may be described as being relatively stiff but still possessing limited flexibility in lateral directions (e.g., resilient or semi-rigid). The dart electrode 12 may be configured to pierce through one or more tissue layers to position the tip electrode element 42 within a desired tissue layer, e.g., the ventricular myocardium. As such, the length or height 47 of the shaft 40 may correspond to the expected pacing site depth. If a second dart electrode 12 is employed, its length or height may be unequal to the expected pacing site depth and may be configured to act as an indifferent electrode for delivery of pacing energy to the tissue.

The one or more fixation members 20 may be described as one or more "tines" having a normally-curved position. The tines may be held in a distally extended position within a delivery tool. The distal tips of tines may penetrate the heart tissue to a limited depth before elastically curving back proximally into the normally curved position (shown) upon release from the delivery tool.

In some examples, the distal fixation and electrode assembly 36 includes a distal housing-based electrode 22. In the case of using the device 400 as a pacemaker for multiple chamber pacing (e.g., dual or triple chamber pacing) and sensing, the tip electrode element 42 may be used as a cathode electrode paired with the proximal housing-based electrode 24 serving as a return anode electrode. Alternatively, the distal housing-based electrode 22 may serve as a return anode electrode paired with tip electrode element 42 for sensing ventricular signals and delivering ventricular pacing pulses. In other examples, the distal housing-based electrode 22 may be a cathode electrode for sensing atrial signals and delivering pacing pulses to the atrial myocardium in the target implant region 4. When the distal housing-based electrode 22 serves as an atrial cathode electrode, the proximal housing-based electrode 24 may serve as the return anode paired with the tip electrode element 42 for ventricular pacing and sensing and as the return anode paired with the distal housing-based electrode 22 for atrial pacing and sensing.

As shown in this illustration, the target implant region 4 in some pacing applications is along the atrial endocardium 18, generally inferior to the AV node 15 and the His bundle 5. The dart electrode 42 may define the length or height 47 of the shaft 40 for penetrating through the atrial endocardium 18 in the target implant region 4, through the central fibrous body 16, and into the ventricular myocardium 14 without perforating through the ventricular endocardial surface 17. When the length or height 47 of the dart electrode 12 is fully advanced into the target implant region 4, the tip electrode element 42 may rest, or be positioned, within the ventricular myocardium 14, and the distal housing-based electrode 22 may be positioned in intimate contact with or close proximity to the atrial endocardium 18.

The device 400 may include a motion sensor 11, or motion detector, within the housing 30. The motion sensor 11 may be used to monitor mechanical activity, such as atrial mechanical activity (e.g., an atrial contraction) and/or ventricular mechanical activity (e.g., a ventricular contraction). In some embodiments, the motion sensor 11 may be used to detect RA mechanical activity. A non-limiting example of a motion sensor 11 includes an accelerometer. In some embodiments, the mechanical activity detected by the motion sensor 11 may be used to supplement or replace electrical activity detected by one or more of the electrodes of the device 400. For example, the motion sensor 11 may be used in addition to, or as an alternative to, the proximal housing-based electrode 24.

The mechanical activity detected by the motion sensor 11 may correspond to various heart sounds. In general, heart sounds are associated with mechanical vibrations of a patient's heart and the flow of blood through the heart valves and, thus, may be highly correlated with pressure gradients across heart valves and blood pressure. Heart sounds may be not only due to vibrations of and pressure within the heart, but may also be due to the entire cardiohemic system, e.g., blood, heart, great arteries, etc. Heart sounds may recur with each cardiac cycle and are separated and classified according to the activity associated with the vibration.

The device 400 may be implanted such that the electrode 12 is positioned to sense electrical activity or deliver pacing therapy to a specific part of the patient's LV myocardium. For example, the electrode 12 may be implanted in the basal, septal, or basal-septal region of the LV.

Figure 9:
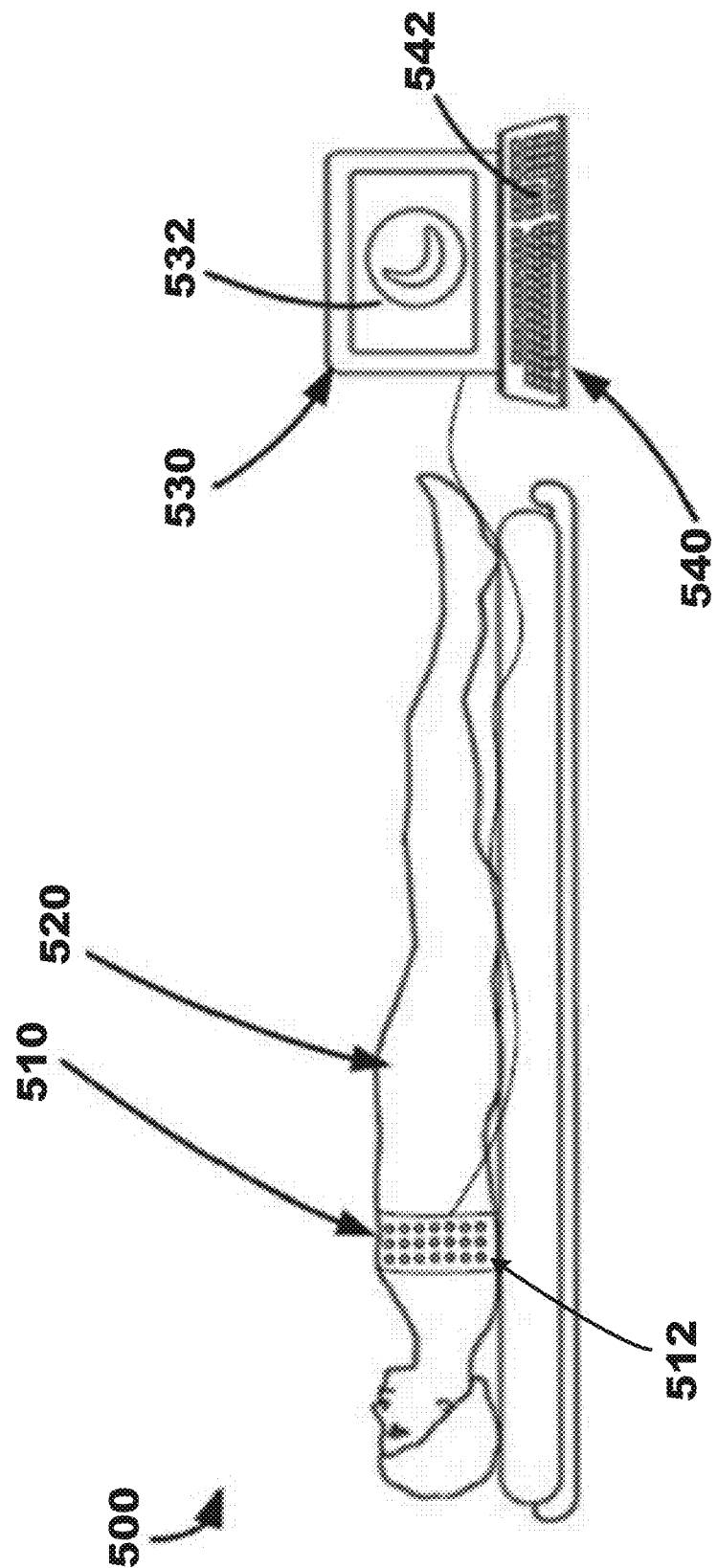
FIG. 9 is a diagram of an external apparatus including electrode apparatus, display apparatus, and computing apparatus for use with, for example, the system of FIG. 7, the device of FIG. 8, and the methods of FIGS. 1-5.

FIG. 9 shows one example of an external apparatus may be used to facilitate implantation or configuration of an implantable lead or device. FIG. 9 depicts one example of a system 500 of the external apparatus including electrode apparatus 510, display apparatus 530, and computing apparatus 540, in use with a patient 520.

The electrode apparatus 510 as shown includes a plurality of electrodes 512 incorporated, or included, within a band wrapped around the chest, or torso, of a patient 520. In other embodiments, the electrode apparatus 510 may include a vest upon which the plurality of electrodes 512 may be attached, or to which the electrodes 512 may be coupled. The electrode apparatus 510 is operatively coupled to the computing apparatus 540 (e.g., through one or wired electrical connections, wirelessly, etc.) to provide electrical signals from each of the electrodes to the computing apparatus 540 for analysis, evaluation, etc. Electrode apparatus may be described in U.S. Pat. No. 9,320,446 entitled "Bioelectric Sensor Device and Methods" and issued on Apr. 26, 2016, which is incorporated herein by reference in its entirety.

Although not described herein, the system 500 may further include imaging apparatus (not shown). The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools, such as an imaging agent. It is to be understood that the systems, methods, and interfaces described herein may further use imaging apparatus to provide noninvasive assistance to a user (e.g., a physician) to calibrate and/or deliver a cardiac pacing therapy, to locate and position a device to deliver cardiac pacing therapy, and/or to locate or select a pacing electrode or pacing vector proximate the patient's heart for cardiac pacing therapy in conjunction with the evaluation of cardiac pacing therapy.

For example, the systems, methods, and interfaces may provide image-guided navigation that may be used to navigate leads including leadless devices, electrodes, leadless electrodes, wireless electrodes, catheters, etc., within the patient's body while also providing noninvasive cardiac therapy evaluation including determining whether a paced setting is optimal or determining whether one or more selected parameters are optimal, such as selected location information (e.g., location information for the electrodes to target a particular location in the left ventricle). Systems and methods that use imaging apparatus and/or electrode apparatus may be described in U.S. Pat. No. 9,877,789 issued on Jan. 30, 2018, and entitled "Implantable Electrode Location Selection," U.S. Pat. No. 10,251,555 issued Apr. 9, 2019, and entitled "Implantable Electrode Location Selection," U.S. Pat. No. 9,924,884 issued on Mar. 27, 2018, and entitled "Systems, Methods, and Interfaces for Identifying Effective Electrodes," U.S. Pat. No. 10,064,567 issued on Sep. 4, 2018, and entitled "Systems, Methods, and Interfaces for Identifying Optical-Electrical Vectors," each of which is incorporated herein by reference in its entirety.

Imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MM), high frequency ultrasound (HIFU), optical coherence tomography (OCT), intravascular ultrasound (IVUS), two-dimensional (2D) ultrasound, three dimensional (3D) ultrasound, four-dimensional (4D) ultrasound, intraoperative CT, intraoperative MM, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate treatment apparatus proximate target locations (e.g., such as locations within the RA or LV) within the heart or other areas of interest.

Systems and/or imaging apparatus that may be used in conjunction with the exemplary systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. No. 8,731,642 issued May 20, 2014, to Zarkh et al. U.S. Pat. No. 8,861,830 issued Oct. 14, 2014, to Brada et al., U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al.

issued on Mar. 19, 2013, each of which is incorporated herein by reference in its entirety.

The display apparatus 530 and the computing apparatus 540 may be configured to display and analyze data such as, e.g., electrical signals (e.g., electrocardiogram data), cardiac information representative of one or more of mechanical cardiac functionality and electrical cardiac functionality (e.g., mechanical cardiac functionality only, electrical cardiac functionality only, or both mechanical cardiac functionality and electrical cardiac functionality), etc. Cardiac information may include, e.g., electrical heterogeneity information or electrical dyssynchrony information, surrogate electrical activation information or data, etc. that is generated using electrical signals gathered, monitored, or collected, using the electrode apparatus 510. The computing apparatus 540 may be a server, a personal computer, or a tablet computer. The computing apparatus 540 may be configured to receive input from input apparatus 542 and transmit output to the display apparatus 530. Further, the computing apparatus 540 may include data storage that may allow for access to processing programs or routines and/or one or more other types of data, e.g., for calibrating and/or delivering pacing therapy for driving a graphical user interface configured to noninvasively assist a user in targeting placement of a pacing device, and/or for evaluating pacing therapy at that location (e.g., the location of an implantable electrode used for pacing, the location of pacing therapy delivered by a particular pacing vector, etc.).

The computing apparatus 540 may be operatively coupled to the input apparatus 542 and the display apparatus 530 to, e.g., transmit data to and from each of the input apparatus 542 and the display apparatus 530. For example, the computing apparatus 540 may be electrically coupled to each of the input apparatus 542 and the display apparatus 530 using, e.g., analog electrical connections, digital electrical connections, wireless connections, bus-based connections, network-based connections, internet-based connections, etc. As described further herein, a user may provide input to the input apparatus 542 to manipulate, or modify, one or more graphical depictions displayed on the display apparatus 530 and to view and/or select one or more pieces of information related to the cardiac therapy.

Although as depicted the input apparatus 542 is a keyboard, it is to be understood that the input apparatus 542 may include any apparatus capable of providing input to the computing apparatus 540 for performing the functionality, methods, and/or logic described herein. For example, the input apparatus 542 may include a mouse, a trackball, a touchscreen (e.g., capacitive touchscreen, a resistive touchscreen, a multi-touch touchscreen, etc.), etc. Likewise, the display apparatus 530 may include any apparatus capable of displaying information to a user, such as a graphical user interface 532 including cardiac information, textual instructions, graphical depictions of electrical activation information, graphical depictions of anatomy of a human heart, images or graphical depictions of the patient's heart, graphical depictions of a leadless pacing device used to calibrate and/or deliver pacing therapy, graphical depictions of a leadless pacing device being positioned or placed to provide cardiac pacing therapy, graphical depictions of locations of one or more electrodes, graphical depictions of a human torso, images or graphical depictions of the patient's torso, graphical depictions or actual images of implanted electrodes and/or leads, etc. Further, the display apparatus 530 may include a liquid crystal display, an organic light-emitting diode screen, a touchscreen, a cathode ray tube display, etc.

The processing programs or routines stored and/or executed by the computing apparatus 540 may include programs or routines for computational mathematics, matrix mathematics, dispersion determinations (e.g., standard deviations, variances, ranges, interquartile ranges, mean absolute differences, average absolute deviations, etc.), filtering algorithms, maximum value determinations, minimum value determinations, threshold determinations, moving windowing algorithms, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more methods and/or processes described herein. Data stored and/or used by the computing apparatus 540 may include, for example, electrical signal/waveform data from the electrode apparatus 510, dispersions signals, windowed dispersions signals, parts or portions of various signals, electrical activation times from the electrode apparatus 510, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

Electrical activation times of the patient's heart may be useful to evaluate a patient's cardiac condition and/or to calibrate, deliver, or evaluate cardiac therapy to be or being delivered to a patient. Surrogate electrical activation information or data of one or more regions of a patient's heart may be monitored, or determined, using the electrode apparatus 510. The electrode apparatus 510 may be configured to measure body-surface potentials of a patient 520 and, more particularly, torso-surface potentials of the patient 520.

The electrodes 512 may be configured to surround the heart of the patient 520 and record, or monitor, the electrical signals associated with the depolarization and repolarization of the heart after the signals have propagated through the torso of a patient 520. Each of the electrodes 512 may be used in a unipolar configuration to sense the torso-surface potentials that reflect the cardiac signals. The interface/amplifier circuitry 516 may also be coupled to a return or indifferent electrode (not shown) that may be used in combination with each electrode 512 for unipolar sensing. In some examples, there may be about 12 to about 50 electrodes 512 spatially distributed around the torso of the patient. Other configurations may have more or fewer electrodes 512.

The computing apparatus 540 may record and analyze the electrical activity (e.g., torso-surface potential signals) sensed by electrodes 512. The computing apparatus 540 may be configured to analyze the signals from the electrodes 512 to provide as anterior and posterior electrode signals and surrogate cardiac electrical activation times, e.g., representative of actual, or local, electrical activation times of one or more regions of the patient's heart as will be further described herein. The computing apparatus 540 may be configured to analyze the signals from the electrodes 512 to provide as anterior-septal electrode signals and surrogate cardiac electrical activation times, e.g., representative of actual, or local, electrical activation times of one or more anterior-septal regions of the patient's heart, as will be further described herein, e.g., for use in calibrating, delivering, and/or evaluating pacing therapy. Further, the electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. Measurement of activation times can be performed by measuring the period of time between an onset of cardiac depolarization (e.g., onset of QRS complex) and an appropriate fiducial point such as, e.g., a peak value, a minimum value, a minimum slope, a maximum slope, a zero crossing, a threshold crossing, etc.

Additionally, the computing apparatus 540 may be configured to provide graphical user interfaces depicting the surrogate electrical activation times obtained using the electrode apparatus 510. Systems, methods, and/or interfaces may noninvasively use the electrical information collected using the electrode apparatus 510 to evaluate a patient's cardiac condition and/or to calibrate, deliver, or evaluate cardiac pacing therapy to be or being delivered to the patient.

As described herein, the electrode apparatus 510 may be configured to measure electrical information (e.g., electrical signals) representing different regions of a patient's heart. For example, activation times of different regions of a patient's heart can be approximated from surface electrocardiogram (ECG) activation times measured using surface electrodes in proximity to surface areas corresponding to the different regions of the patient's heart. In at least one example, activation times of the anterior-septal region of a patient's heart can be approximated from surface ECG activation times measured using surface electrodes in proximity to surface areas corresponding to the anterior-septal region of the patient's heart. That is, a portion of the set of electrodes 512, and not the entire set, can be used to generate activation times corresponding to a particular location of the patient's heart that the portion of the set of electrodes corresponds to.

The systems, methods, and interfaces may be used to provide noninvasive assistance to a user in the evaluation of a patient's cardiac health or status, and/or the evaluation of cardiac therapy such as CRT by use of the electrode apparatus 510 (e.g., cardiac therapy being presently-delivered to a patient during implantation or after implantation). Further, the systems, methods, and interfaces may be used to assist a user in the configuration, or calibration, of the cardiac therapy, such as CRT, to be or being delivered to a patient.

Electrical activity may be monitored using a plurality of external electrodes, such as electrodes 512. The electrical activity can be monitored by a plurality of electrodes during pacing therapy or in the absence of pacing therapy. The monitored electrical activity can be used to evaluate pacing therapy to a patient. The electrical activity monitored using the ECG belt described can be used to evaluate at least one paced setting of the pacing therapy on the heart. As an example, a paced setting can be any one parameter or a combination of parameters including, but not limited to, electrode position, pacing polarity, pacing output, pacing pulse width, timing at which ventricular pacing is delivered relative to atrial timing, pacing rate, etc. Further, as an example, the location of the leadless device or a pacing lead can include a location in the right ventricle, left ventricle, or right atrium.

Further, body-surface isochronal maps of ventricular activation can be constructed using the monitored electrical activity during pacing therapy or in the absence of pacing therapy. The monitored electrical activity and/or the map of ventricular activation can be used to generate electrical heterogeneity information (EHI). The electrical heterogeneity information can include determining metrics of electrical heterogeneity. The metrics of electrical heterogeneity can include a metric of standard deviation of activation times (SDAT) of electrodes on a left side of a torso of the patient and/or a metric of mean left ventricular activation time (LVAT) of electrodes on the left side of the torso of the patient. A metric of LVAT may be determined from electrodes on both the anterior and posterior surfaces, which are more proximal to the left ventricle. The metrics of electrical heterogeneity information can include a metric of mean right ventricular activation time (RVAT) of electrodes on the right side of the torso of the patient. A metric of RVAT may be determined from electrodes on both the anterior and posterior surfaces which are more proximal to the right ventricle. The metrics of electrical heterogeneity can include a metric of mean total activation time (mTAT) taken from a plurality of electrode signals from both sides of the torso of the patient, or it may include other metrics (e.g., standard deviation, interquartile deviations, a difference between a latest activation time and earliest activation time) reflecting a range or dispersion of activation times on a plurality of electrodes located on the right side of the patient torso or left side of the patient torso, or combining both right and left sides of the patient torso. The metrics of electrical heterogeneity information can include a metric of anterior-septal activation times (ASAT) of electrodes on the torso in close proximity to the anterior-septal portion of the heart.

Electrical heterogeneity information (EHI) may be generated during delivery of pacing therapy at one or more paced settings. The electrical heterogeneity information can be generated using metrics of electrical heterogeneity. As an example, the metrics of electrical heterogeneity can include one or more of an SDAT, an LVAT, an RVAT, an mTAT, and an ASAT. In another example, only ASAT may be determined and further used, and/or ASAT may be more heavily weighted than other values.

One or more paced settings associated with the pacing therapy may be evaluated. A paced setting can include a plurality of pacing parameters. The plurality of pacing parameters can be optimal if the patient's cardiac condition improves, if the pacing therapy is effectively capturing a desired portion of the RA, RV, or LV, and/or if a metric of electrical heterogeneity improves by a certain threshold compared to a baseline rhythm or therapy. The determination of whether the paced setting is optimal can be based on at least one metric of electrical heterogeneity generated from electrical activity during pacing (and also, in some cases, during native conduction, or in the absence of pacing). The at least one metric can include one or more of an SDAT, an LVAT, an RVAT, an mTAT, and an ASAT.

Further, the plurality of pacing parameters can be optimal if a metric of electrical heterogeneity is greater than or less than a particular threshold, and/or if the location of the pacing therapy to excite the left ventricle causes a particular pattern of excitation of the muscle fibers in the heart. In addition, the plurality of pacing parameters can be optimal if a metric of electrical heterogeneity indicates a correction of a left bundle branch block (LBBB), and/or if a metric of electrical heterogeneity indicates a complete engagement of a Purkinje system, etc. As an example, a metric of electrical heterogeneity of an ASAT less than or equal to a threshold (e.g., a threshold of 30 ms) and an LVAT less than or equal to a threshold (e.g., a threshold of 30 ms) can indicate a correction of an LBBB, and thus, the paced setting is optimal. As an example, a metric of electrical heterogeneity of an RVAT less than or equal to a threshold (e.g., a threshold of 30 ms), an ASAT less than or equal to a threshold (e.g., a threshold of 30 ms), and an LVAT less than or equal to a threshold (e.g., a threshold of 30 ms) can indicate a complete engagement of the Purkinje system, and thus the paced setting is may be optimal.

The paced setting can be determined to be optimal in response to the pacing therapy using the paced setting being acceptable, being beneficial, being indicative of complete engagement of patient's native cardiac conduction system, being indicative of correction of a ventricular conduction disorder (e.g., left bundle branch block), etc. A paced setting can include one or more of a pacing electrode position (including one or more of a depth, an angle, an amount of turn for a screw-based fixation mechanism, etc.), a voltage, a pulse width, an intensity, a pacing polarity, a pacing vector, a pacing waveform, a timing of the pacing delivered relative to an intrinsic or paced atrial event or relative to the intrinsic His bundle potential, and/or a pacing location, etc. A pacing vector can include any two or more pacing electrodes such as, e.g., a tip electrode to a can electrode, a tip electrode to a ring electrode etc., that are used to deliver the pacing therapy, etc. The pacing location can refer to the location of any of the one or more pacing electrodes that are positioned using a lead, a leadless device, and/or any device or apparatus configured to deliver pacing therapy.

A paced setting for therapy may be adjusted. The paced setting can be adjusted in response to the paced setting being not optimal. The paced setting can be adjusted in response to the paced setting being within an optimal range but in order to determine whether the paced setting can be at a position within the optimal range that is more beneficial, more useful, more functional, etc., for the pacing therapy. The paced setting could be adjusted to find the most optimal metric of electrical heterogeneity.

A determination of whether the paced setting is optimal can be based on a particular metric of electrical heterogeneity using an ECG belt. In at least one example, the paced setting can be adjusted at intervals that correlate with a change in the metric of electrical heterogeneity until the metric of electrical heterogeneity is at or proximate a particular metric value. For instance, the adjusting of the paced setting can cause the metric of electrical heterogeneity to approach a particular threshold metric of electrical heterogeneity and, as the metric approaches the particular threshold, the rate at which the paced setting is adjusted can be slowed down. Put another way, as the metric of electrical heterogeneity is further from the particular threshold metric, the paced setting can be adjusted more quickly and as the metric of electrical heterogeneity gets closer to the particular threshold metric, the paced setting can be adjusted more slowly until the metric of electrical heterogeneity is at the particular threshold metric.

During implantation, various techniques may be used to determine whether the correct target implant region 4 has been reached in the triangle of Koch region before attempting to implant the IMD. In some embodiments, the target implant region 4 may be identified using a slow pathway signal measured using a tip of a mapping electrode of a delivery assembly or delivery catheter. In some embodiments, the target implant region 4 may be identified by testing pacing output with a tip of a mapping electrode of a delivery assembly or delivery catheter and stepping down the pacing output until a virtual ventricular to atrial pacing transit ECG pattern is detected. Using such techniques to appropriately identify the target implant region 4 before introducing the IMD may facilitate the overall implantation process.

Figure 10:
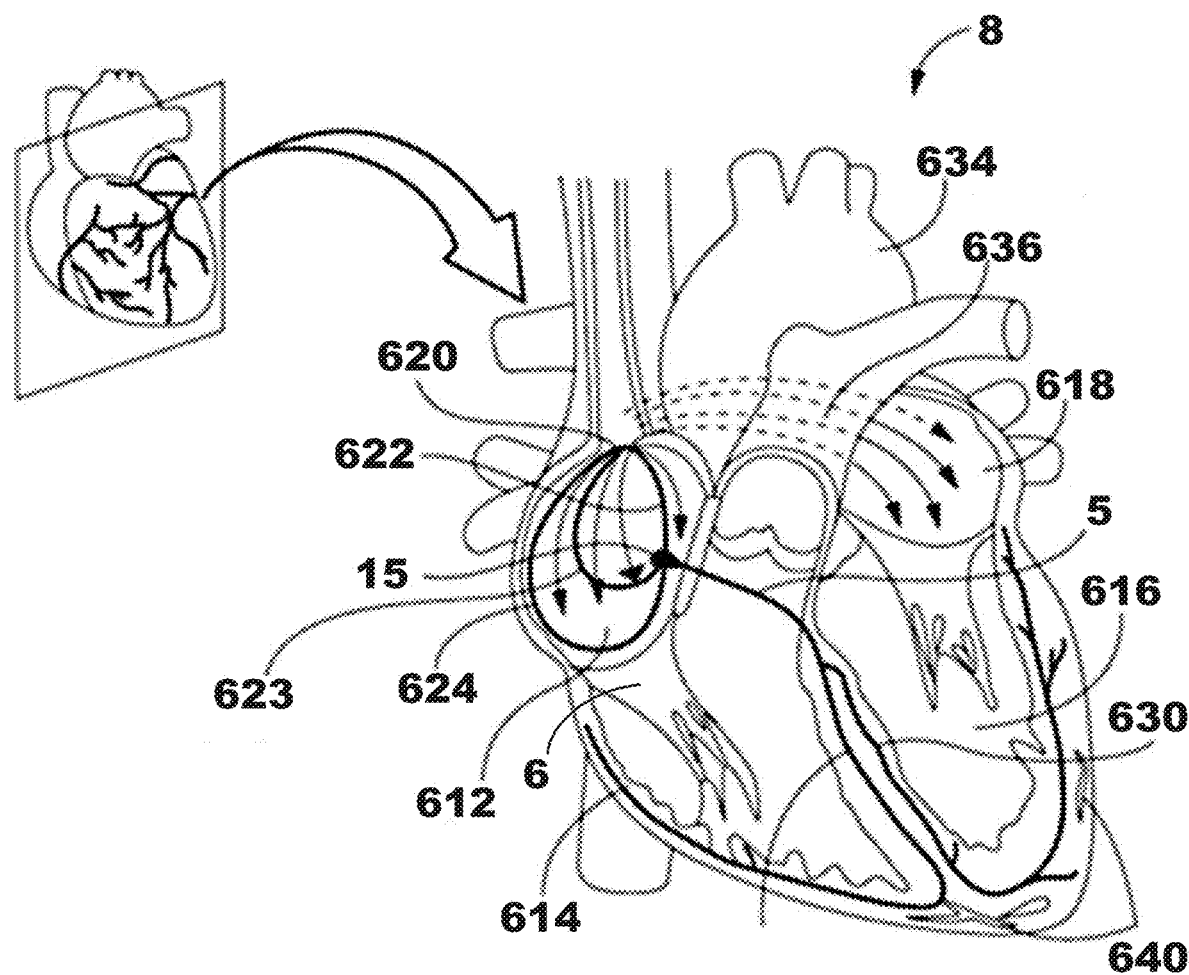
FIG. 10 is a diagram that illustrates various structures of the patient's heart.

With reference to FIG. 10, pacing techniques generally involve pacing one or more of the four chambers of patient's heart 8, including the right atrium (RA) 612, right ventricle (RV) 614, left ventricle (LV) 616, and left atrium (LA) 618 all of which are shown in the anterior view of a frontal section of patient's heart 8. Some therapeutic pacing techniques involve the cardiac conduction system. The cardiac conduction system, like a "superhighway," may be described as quickly conducting electrical pulses whereas pacing cardiac muscle tissue may slowly conduct electrical pulses, like "traveling on a dirt road." The cardiac conduction system includes SA node 620, atrial internodal tracts 622, 623, 624 (i.e., anterior internodal 622, middle internodal 623, and posterior internodal 624), AV node 15, His bundle 5 (also known as the atrioventricular bundle or bundle of His), and bundle branches including the left bundle branch (LBB) 630 and the right bundle branch (RBB) 632. FIG. 10 also shows the arch of aorta 634 and Bachman's bundle 636.

The SA node 15, located at the junction of the superior vena cava (SVC) 638 and RA 612, is considered to be the natural pacemaker of the heart since it continuously and repeatedly emits electrical impulses. The electrical impulse spreads through the muscles of RA 612 to LA 618 to cause synchronous contraction of the atria. Electrical impulses are also carried through atrial internodal tracts to AV node 15—the sole connection between the atria and the ventricles.

Conduction through the tissue of the AV node 15 takes longer than through the atrial tissue, resulting in a delay between atrial contraction and the start of ventricular contraction. The AV delay, which is the delay between atrial contraction and ventricular contractor, allows the atria to empty blood into the ventricles. Then, the valves between the atria and ventricles close before causing ventricular contraction via branches of the His bundle 5.

His bundle 5 is located in the membranous atrioventricular septum near the annulus of the tricuspid valve. The tricuspid valve 6 is between the RA 612 and the RV 614. His bundle 5 splits into the LBB 630 and RBB 632 and are formed of specialized fibers called "Purkinje fibers" 640. Purkinje fibers 640 may be described as rapidly conducting an action potential down the ventricular septum, spreading the depolarization wavefront quickly through the remaining ventricular myocardium, and producing a coordinated contraction of the ventricular muscle mass.

Figure 11:
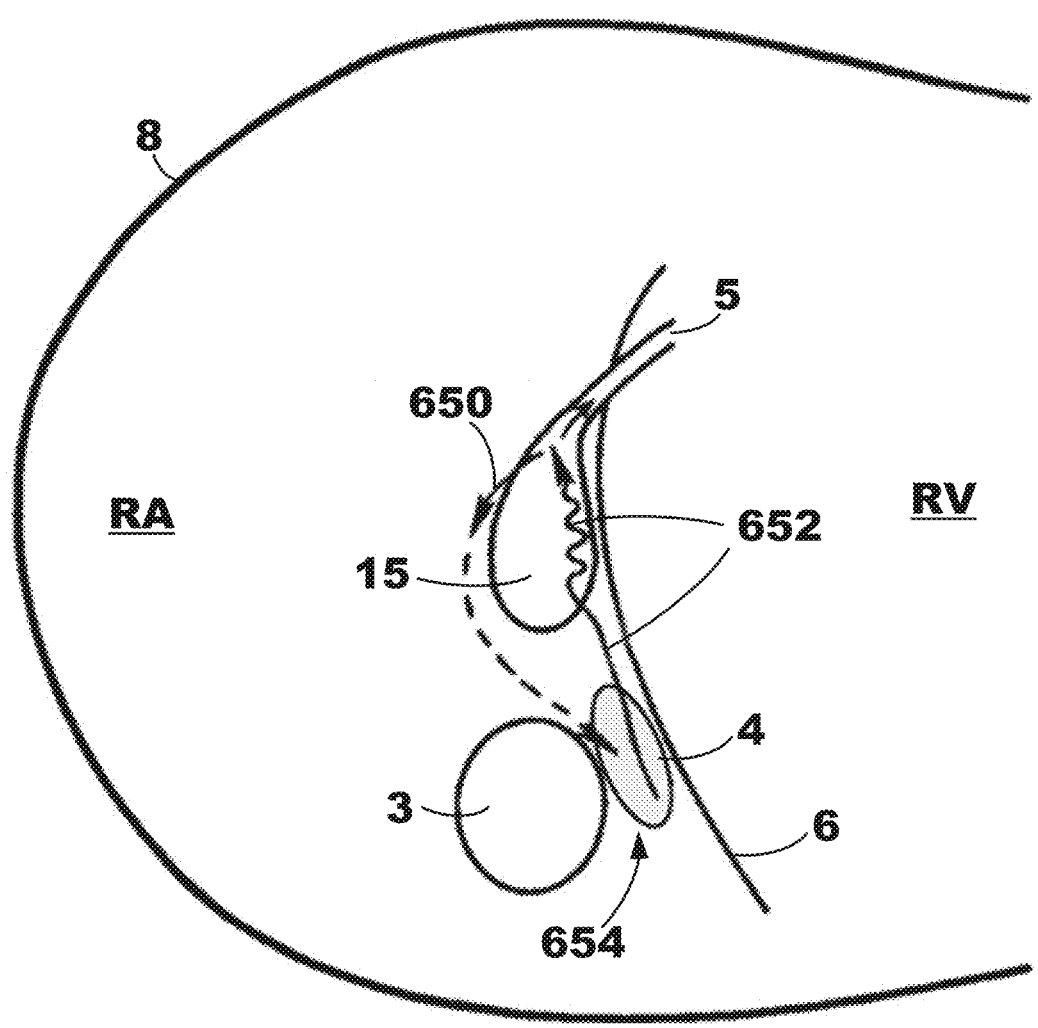
FIG. 11 is a diagram that illustrates particular electrical pathways of the patient's heart usable to detect an atrial slow pathway potential (ASP).

FIG. 11 is a diagram that illustrates particular electrical pathways of the patient's heart 8 and one example of a target implant region 4 suitable for VfA cardiac therapy. In the illustrated embodiment, the patient's heart 8 defines a fast pathway 650 from the AV node 15 to the target implant region 4, which may be described as part of the conduction system of the heart 8. The patient's heart 8 also defines a slow pathway 652 from the target implant region 4 to the AV node 15, which may also be described as part of the cardiac tissue. The target implant region 4 may also be described as the slow path area. The target implant region 4 may be determined to be suitable based upon electrical signals indicating the ASP is detected. Detection of the ASP may indicate that the target implant region 4 within the triangle of Koch region 654 has been reached using an electrode.

Figure 12:
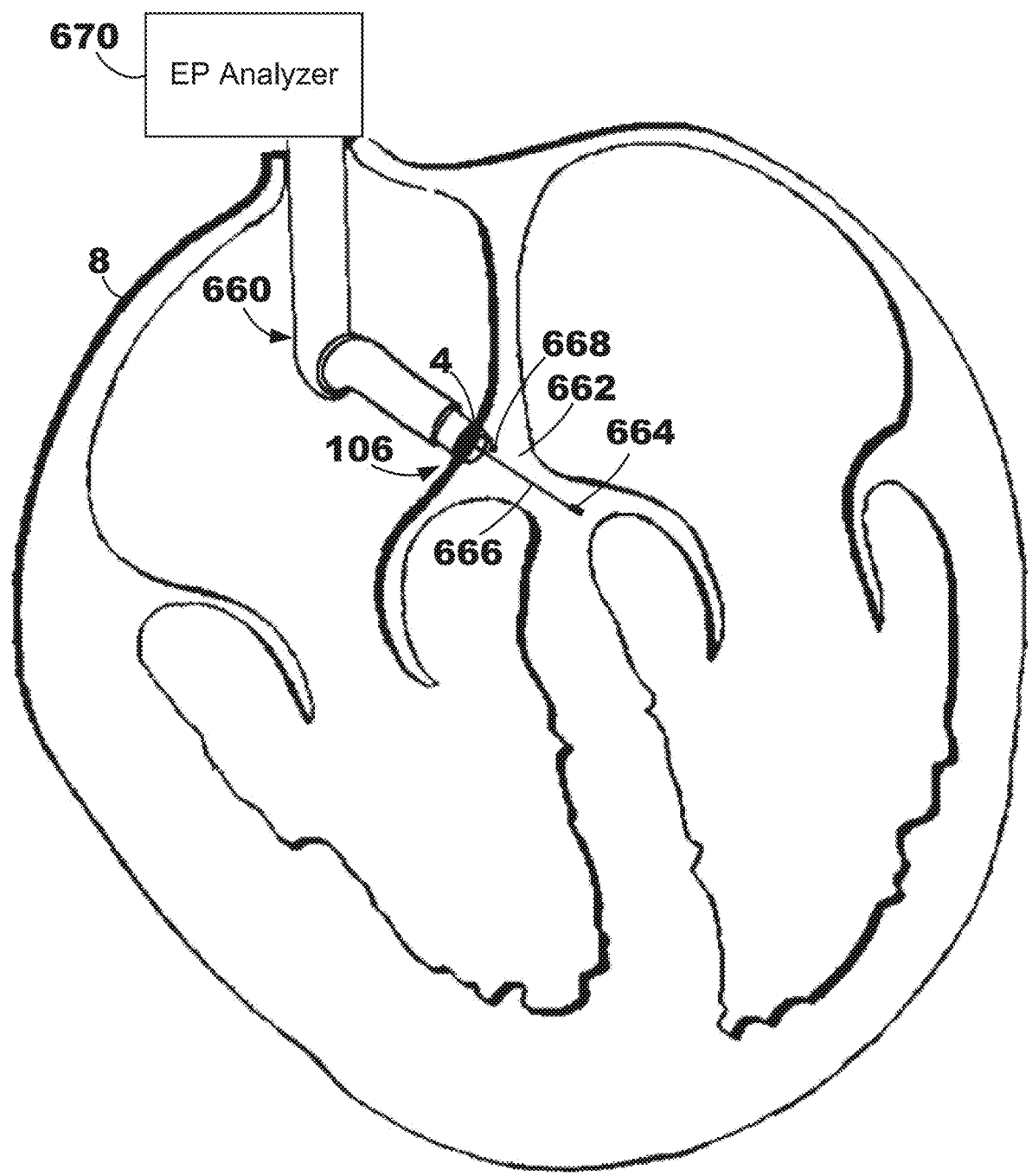
FIG. 12 is a conceptual diagram that illustrates a delivery assembly usable to detect the ASP for use with, for example, the methods of FIGS. 1-5, the system of FIG. 7, the device of FIG. 8, and the apparatus of FIG. 9.

FIG. 12 is a conceptual diagram that illustrates one example of a delivery assembly 660 fixed to the AV septal wall 662 of the patient's heart 8, which may be used to implant a leaded or leadless IMD. The delivery assembly 660 may be described as a delivery catheter. The delivery assembly 660 may include a mapping electrode 664, which may be inserted into the AV septal wall 662 through the target implant region 4 in the triangle of Koch region 106. The mapping electrode 664 may be used to test potential implantation site locations and different depths within the AV septal wall 662, for example, until an ASP is detected.

In some embodiments, the mapping electrode 664 is disposed on a guide wire 666. The guide wire 666 may be described as a mapping guide wire. Additionally, or alternatively, the delivery assembly 660 may include an electrically conductive fixation element on a sheath may be used to provide a mapping electrode 668.

The mapping electrode 664 and the mapping electrode 668 may each be electrically coupled to an individual conductor extending between a distal portion and a proximal portion of the delivery assembly 660. The conductor may be coupled to a proximal contact, such as a proximal end ring, which may be connected to an analyzer 670 to facilitate mapping. In particular, the analyzer 670 may be any suitable electrophysiological (EP) analyzer configured to analyze electrogram (EGM) signals and/or ECG signals for mapping selected by one skilled in the art having the benefit of this disclosure. The analyzer may include a controller having processing circuitry and memory.

In general, any suitable delivery assembly may be used to deliver a leaded or leadless 1 MB. Examples of delivery assemblies that may be used include those described in U.S. Provisional Application No. 62/914,937 (Hine et al.), filed Oct. 14, 2019, and U.S. Provisional Application No. 62/948,366 (Hine et al.), filed Dec. 16, 2019, which are incorporated herein by reference.

Figure 13:
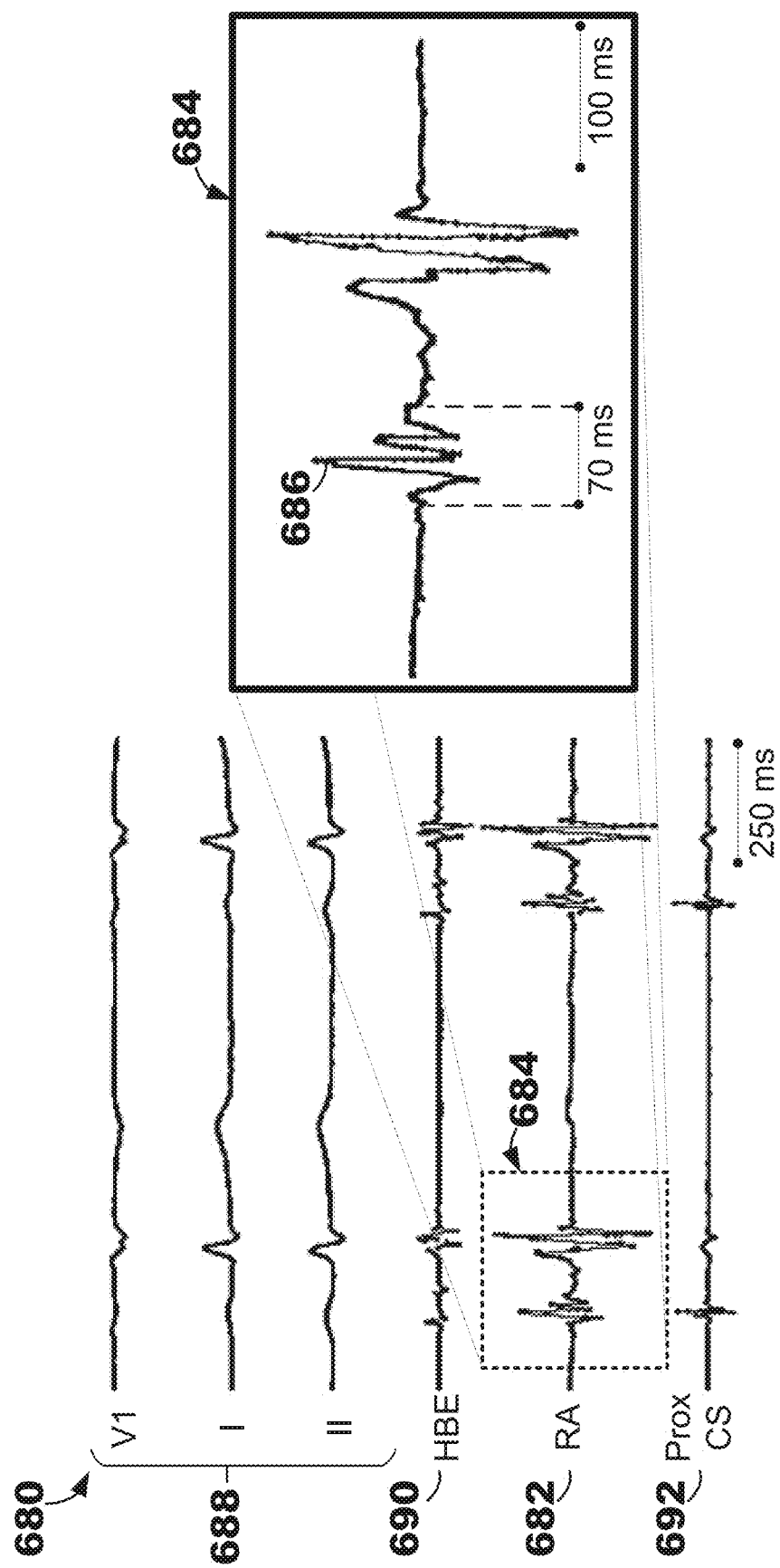
FIG. 13 is a plot that illustrates an EGM signal including an ASP signature waveform usable to determine a target implant region.

FIG. 13 is a plot 680 that illustrates one example of an electrophysiology (EP) mapping signal, or EGM signal 682, which may be measured using an EP analyzer. In particular, a mapping electrode implanted in a target implant region may measure the EGM signal 682. As can be seen, particularly in exploded view of region 684, an ASP signature waveform 686 is detected in the EGM signal 682 may indicate that the mapping electrode is appropriately implanted in a suitable target implant region within the triangle of Koch region.

In some embodiments, the ASP signature waveform 686 may be identified as having multiple deflections. As illustrated, the ASP signature waveform 686 may include four "peaks" (local maxima) and three "valleys" (local minima). Collectively, the local maxima and minima may be described as deflection points. As shown, the ASP signature waveform 686 includes seven deflection points. In general, the ASP waveform 686 may include more local maxima and minima than other waveforms that may be detected in the EGM signal 682.

Other ECG and EGM signals are shown for reference. In the illustrated embodiment, various ECG signals 688 are shown (V1, I, and II) and other EGM signals, such as a His bundle electrode signal 690 and a proximal coronary sinus electrode signal 692. The EGM signal 682 may also be described as an RA electrode signal.

Figure 14:
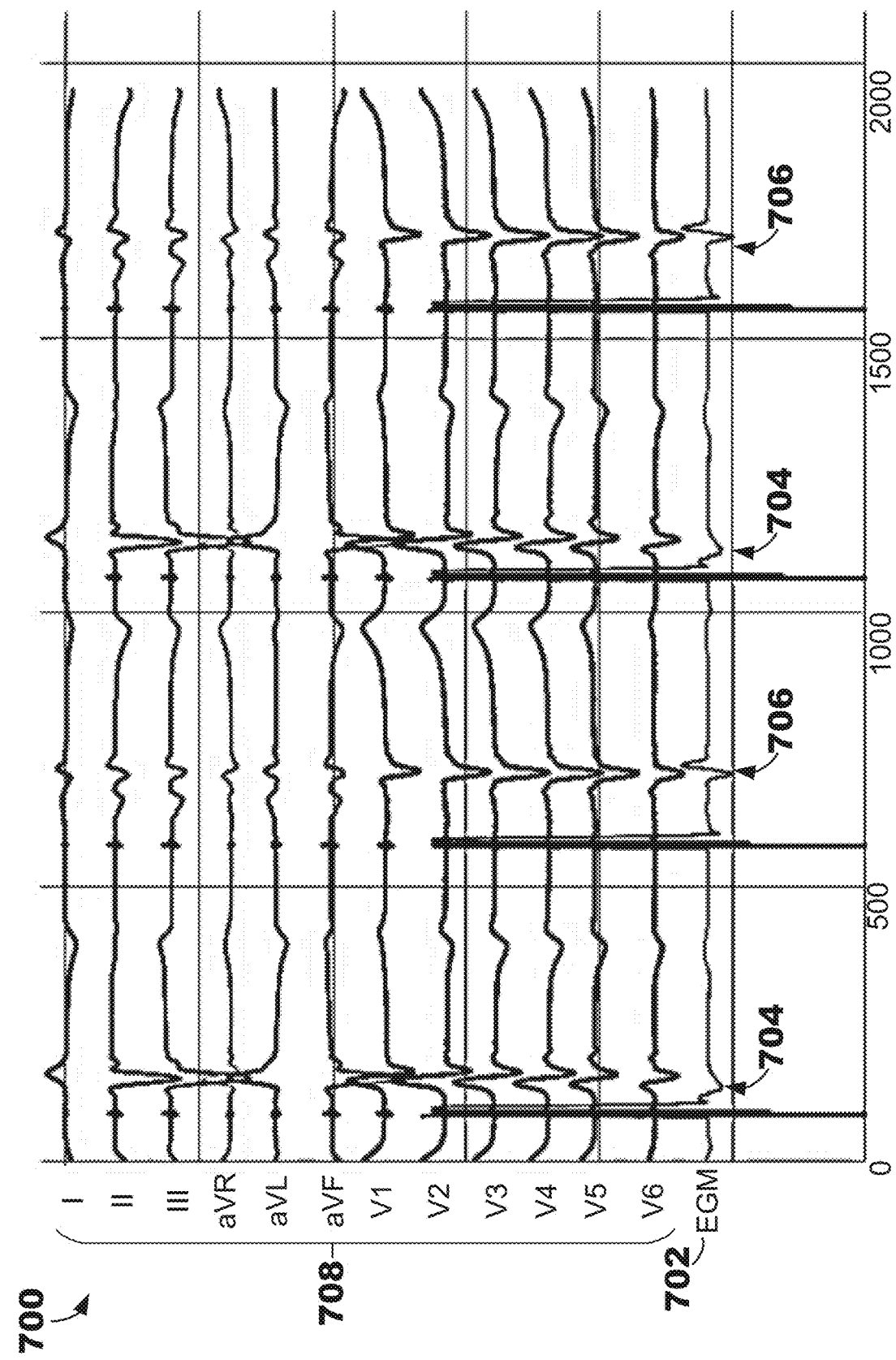
FIG. 14 is a plot that illustrates ECG signals in response to high and low pacing outputs from an EGM pacing pulse usable to determine a target implant region.

FIG. 14 is a plot 700 that illustrates one example of a mapping signal, or EGM signal 702, which includes delivery of test pacing, and various ECG signals 708, which may be used to measure the response to the pacing signal using an EP analyzer. In some embodiments, test pacing pulses may be provided to a potential implant region starting at a higher pacing output, such as 10 volts (V) for 1 ms, and reducing the pacing output to a lower pacing output, such as 0.5 V for 1 ms. The potential implant region may be identified as a suitable target implant region in response to a virtual ventricular to atrial pacing transit ECG pattern is detected in the ECG signals 708.

In the plot 700, test pacing with high pacing outputs around time windows 704 are shown with respect to the EGM signal 702 and corresponding ECG signals 708 measured, which indicate pacing of the ventricle. Test pacing with lower pacing outputs around time windows 706 are shown with respect to the EGM signal 702 and corresponding ECG signals 708 measured, which indicate a virtual ventricular to atrial pacing transit ECG pattern. In general, higher pacing outputs may pace both the ventricle and the atrium, whereas lower pacing outputs capable of pacing only the atrium may be suitable as target implant regions.

Illustrative Embodiments

While the present disclosure is not so limited, an appreciation of various aspects of the disclosure will be gained through a discussion of the specific illustrative embodiments provided below. Various modifications of the illustrative embodiments, as well as additional embodiments of the disclosure, will become apparent herein.

In embodiment A1, a method comprises locating the triangle of Koch region in the right atrium of a patient's heart; securing at least one electrode of an implantable lead or device to cardiac tissue from the triangle of Koch region to deliver ventricle-from-atrium (VfA) cardiac therapy; and testing the location or depth of the at least one electrode to configure VfA cardiac therapy.

In embodiment A2, a method comprises the method according to embodiment A1, further comprising providing an introduction pathway to deliver at least one electrode to the right atrium of the patient's heart.

In embodiment A3, a method comprises the method according to embodiment A2, wherein providing the introduction pathway to the right atrium comprises one or more of:
    locating a vein that leads to the right atrium of the patient's heart;
    creating an entryway into the vein;
    confirming that the entryway goes into the vein; and
    inserting an introducer into the vein through the entryway.

In embodiment A4, a method comprises the method according to any A embodiment, wherein locating the triangle of Koch region comprises one or more of:
    monitoring delivery of the at least one electrode using imaging;
    advancing the implantable lead or device into the right atrium;
    locating the tricuspid valve of the patient's heart using the implantable lead or device; and
    moving the implantable lead or device partially toward the coronary sinus ostium and the atrioventricular node of the patient's heart to reach the triangle of Koch region.

In embodiment A5, a method comprises the method according to embodiment A4, wherein locating the tricuspid valve comprises locating a ridge of the tricuspid valve proximate to the septal wall of the right atrium above the septal leaflet of the tricuspid valve.

In embodiment A6, a method comprises the method according to any embodiment A1-A3, wherein locating the triangle of Koch region comprises one or more of:
- monitoring delivery of the at least one electrode using imaging;
- advancing the implantable lead or device into the right atrium;
- locating the coronary sinus ostium using the implantable lead or device; and
- moving the implantable lead or device partially toward the tricuspid valve and the atrioventricular node to reach the triangle of Koch region.

In embodiment A7, a method comprises the method according to embodiment A6, wherein locating the coronary sinus ostium comprises:
- advancing the implantable medical lead or device into the coronary sinus of the patient's heart; and
- retracting the implantable medical lead or device until a distal end of the implantable medical lead or device reaches the coronary sinus ostium.

In embodiment A8, a method comprises the method according to any A embodiment, wherein securing at least one electrode of the implantable lead or device to cardiac tissue from the triangle of Koch region to deliver VfA cardiac therapy comprises one or more of:
- determining an initial implant location through the triangle of Koch region;
- orienting the implantable lead or device at the initial implant location;
- attaching the implantable lead or device to the initial implant location;
- testing the initial implant location and depth; and
- updating the initial implant location or depth in response to the testing.

In embodiment A9, a method comprises the method according to embodiment A8, wherein orienting the implantable lead or device comprises pointing a distal end of the implantable lead or device toward the left ventricular apex of the patient's heart.

In embodiment A10, a method comprises the method according to embodiment A8 or A9, wherein testing the initial implant location comprises one or more of:
- monitoring electrical activity using one or more electrodes of the implantable lead or device;
- monitoring mechanical activity using a motion sensor of the implantable lead or device; and
- delivering test pulses using one or more electrodes of the implantable lead or device detectable by an external electrode apparatus.

In embodiment A11, a method comprises the method according to any A embodiment, further comprising preparing a patient for VfA cardiac therapy.

In embodiment A12, a method comprises the method according to any A embodiment, wherein securing the at least one electrode of the implantable lead or device to cardiac tissue through the triangle of Koch region does not position the one or more electrodes into the blood volume of the left ventricle of the patient's heart.

In embodiment A13, a method comprises the method according to any A embodiment, wherein securing the at least one electrode of an implantable lead or device to cardiac tissue through the triangle of Koch region comprises advancing the at least one electrode from the triangle of Koch region through the right atrial endocardium and central fibrous body into the left ventricular myocardium of the patient's heart to deliver cardiac therapy to or sense electrical activity of the left ventricle in the basal region, septal region, or basal-septal region of the left ventricular myocardium.

In embodiment A14, a method comprises the method according to any A embodiment, wherein locating the triangle of Koch region in the right atrium of a patient's heart comprises testing whether an atrial slow pathway potential (ASP) is detected at a potential target implant region using at least one electrode of a delivery assembly.

In embodiment A15, a method comprises the method according to embodiment A14, wherein testing whether an ASP is detected comprises determining whether electrical activity detected by the at least one electrode comprises a deflection pattern indicative of ASP.

In embodiment A16, a method comprises the method according to any A embodiment, wherein locating the triangle of Koch region in the right atrium of a patient's heart comprises testing whether a pacing output at a potential target implant region paces the atrium without pacing the ventricle of the patient's heart using at least one electrode of a delivery assembly.

In embodiment A17, a method comprises the method according to embodiment A16, wherein testing whether a pacing output at a potential target implant region comprises:
- delivering a pacing output to capture ventricular pacing; and
- reducing the pacing output until atrial pacing is captured and ventricular pacing is not captured.

In embodiment B1, a delivery assembly comprises:
- a mapping electrode configured to be advanced into a potential target implant region in the triangle of Koch region; and
- a mapping analyzer operably coupled to the mapping electrode configured to determine whether an atrial slow pathway potential (ASP) is detected at the potential target implant region using the mapping electrode.

In embodiment C1, a delivery assembly comprises:
- a mapping electrode configured to be advanced into a potential target implant region in the triangle of Koch region; and
- a mapping analyzer operably coupled to the mapping electrode configured to determine whether a pacing output at a potential target implant region paces the atrium without pacing the ventricle of the patient's heart using at least one electrode of a delivery assembly.

The embodiment of B1 or C1, wherein the mapping analyzer is configured to carry out the method according to any one of embodiments A14 to A17.

Thus, various techniques related to VfA delivery are disclosed. It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entirety for all purposes, except to the extent any aspect directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Terms related to orientation, such as "proximal," "distal," "top," "bottom," "side," and "end," are used to describe relative positions of components and are not meant to limit the absolute orientation of the embodiments contemplated.

As used herein, the term "configured to" may be used interchangeably with the terms "adapted to" or "structured to" unless the content of this disclosure clearly dictates otherwise.

The singular forms "a," "an," and "the" encompass embodiments having plural referents unless its context clearly dictates otherwise.

The phrases "at least one of," "comprises at least one of," and "one or more of" followed by a list refers to any one of the items in the list and any combination of two or more items in the list.

As used herein, "have," "having," "include," "including," "comprise," "comprising" or the like are used in their open-ended sense, and generally mean "including, but not limited to." It will be understood that "consisting essentially of" "consisting of," and the like are subsumed in "comprising," and the like.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

What is claimed is:

1. A method comprising:
   locating the triangle of Koch region in the right atrium of a patient's heart;
   securing at least one electrode of an implantable lead or device to cardiac tissue from the triangle of Koch region to deliver ventricle-from-atrium (VfA) cardiac therapy; and
   testing the location or depth of the at least one electrode to configure VfA cardiac therapy.

2. The method according to claim 1, further comprising providing an introduction pathway to deliver at least one electrode to the right atrium of the patient's heart.

3. The method according to claim 2, wherein providing the introduction pathway to the right atrium comprises one or more of:
   locating a vein that leads to the right atrium of the patient's heart;
   creating an entryway into the vein;
   confirming that the entryway goes into the vein; and
   inserting an introducer into the vein through the entryway.

4. The method according to claim 1, wherein locating the triangle of Koch region comprises one or more of:
   monitoring delivery of the at least one electrode using imaging;
   advancing the implantable lead or device into the right atrium;
   locating the tricuspid valve of the patient's heart using the implantable lead or device; and
   moving the implantable lead or device partially toward the coronary sinus ostium and the atrioventricular node of the patient's heart to reach the triangle of Koch region.

5. The method according to claim 4, wherein locating the tricuspid valve comprises locating a ridge of the tricuspid valve proximate to the septal wall of the right atrium above the septal leaflet of the tricuspid valve.

6. The method according to claim 1, wherein locating the triangle of Koch region comprises one or more of:
   monitoring delivery of the at least one electrode using imaging;
   advancing the implantable lead or device into the right atrium;
   locating the coronary sinus ostium using the implantable lead or device; and
   moving the implantable lead or device partially toward the tricuspid valve and the atrioventricular node to reach the triangle of Koch region.

7. The method according to claim 6, wherein locating the coronary sinus ostium comprises:
   advancing the implantable medical lead or device into the coronary sinus of the patient's heart; and
   retracting the implantable medical lead or device until a distal end of the implantable medical lead or device reaches the coronary sinus ostium.

8. The method according to claim 1, wherein securing at least one electrode of the implantable lead or device to cardiac tissue from the triangle of Koch region to deliver VfA cardiac therapy comprises one or more of:
   determining an initial implant location through the triangle of Koch region;
   orienting the implantable lead or device at the initial implant location;
   attaching the implantable lead or device to the initial implant location;
   testing the initial implant location and depth; and
   updating the initial implant location or depth in response to the testing.

9. The method according to claim 8, wherein orienting the implantable lead or device comprises pointing a distal end of the implantable lead or device toward the left ventricular apex of the patient's heart.

10. The method according to claim 8, wherein testing the initial implant location comprises one or more of:

monitoring electrical activity using one or more electrodes of the implantable lead or device;

monitoring mechanical activity using a motion sensor of the implantable lead or device; and delivering test pulses using one or more electrodes of the implantable lead or device detectable by an external electrode apparatus.

11. The method according to claim 1, further comprising preparing a patient for VfA cardiac therapy.

12. The method according to claim 1, wherein securing the at least one electrode of the implantable lead or device to cardiac tissue through the triangle of Koch region does not position the one or more electrodes into the blood volume of the left ventricle of the patient's heart.

13. The method according to claim 1, wherein securing the at least one electrode of an implantable lead or device to cardiac tissue through the triangle of Koch region comprises advancing the at least one electrode from the triangle of Koch region through the right atrial endocardium and central fibrous body into the left ventricular myocardium of the patient's heart to deliver cardiac therapy to or sense electrical activity of the left ventricle in the basal region, septal region, or basal-septal region of the left ventricular myocardium.

14. The method according to claim 1, wherein locating the triangle of Koch region in the right atrium of a patient's heart comprises testing whether an atrial slow pathway potential (ASP) is detected at a potential target implant region using at least one electrode of a delivery assembly.

15. The method of claim 14, wherein testing whether an ASP is detected comprises determining whether electrical activity detected by the at least one electrode comprises a deflection pattern indicative of ASP.

16. The method according to claim 1, wherein locating the triangle of Koch region in the right atrium of a patient's heart comprises testing whether a pacing output at a potential target implant region paces the atrium without pacing the ventricle of the patient's heart using at least one electrode of a delivery assembly.

17. The method according to claim 16, wherein testing whether a pacing output at a potential target implant region comprises:

delivering a pacing output to capture ventricular pacing; and reducing the pacing output until atrial pacing is captured and ventricular pacing is not captured.

18. A delivery assembly comprising:

a mapping electrode configured to be advanced into a potential atrial pacing target implant region in the triangle of Koch region, the potential atrial pacing target implant region being a location to pace the right atrium; and a mapping analyzer operably coupled to the mapping electrode configured to determine whether an atrial slow pathway potential (ASP) is detected at the potential atrial pacing target implant region using the mapping electrode.

19. A delivery assembly comprising:

a mapping electrode configured to be advanced into a potential target implant region in the triangle of Koch region; and a mapping analyzer operably coupled to the mapping electrode configured to determine whether a pacing output at a potential target implant region paces the atrium without pacing the ventricle of the patient's heart using at least one electrode of a delivery assembly.

20. The delivery assembly of claim 19, wherein to determine whether a pacing output at a potential target implant region paces the atrium without pacing the ventricle, the mapping analyzer is further configured to:

deliver a pacing output to capture ventricular pacing; and reduce the pacing output until atrial pacing is captured and ventricular pacing is not captured.

\* \* \* \* \*